US012708489B2

(12) United States Patent
Grebenkin et al.

(10) Patent No.: US 12,708,489 B2
(45) Date of Patent: Aug. 18, 2026

(54) METHODS AND APPARATUSES FOR TREATMENT QUALITY ASSESSMENT

(71) Applicant: Align Technology, Inc., San Jose, CA (US)

(72) Inventors: Sergey Grebenkin, Madrid (ES); Victoria Bogina, Bashkortostan (RU); Amarendra Thummeti, Livermore, CA (US); Mitra Derakhshan, Herndon, VA (US); Jeeyoung Choi, Sunnyvale, CA (US); Christopher E. Cramer, Durham, NC (US); Zalina Nurmukhametova, Moscow (RU); Ilfat Sabirov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 193 days.

(21) Appl. No.: 18/480,483

(22) Filed: Oct. 3, 2023

(65) Prior Publication Data

US 2024/0108436 A1 Apr. 4, 2024

Related U.S. Application Data

(60) Provisional application No. 63/412,871, filed on Oct. 3, 2022.

(51) Int. Cl.

*A61C 7/00* (2006.01)
*A61C 7/08* (2006.01)
*G16H 50/50* (2018.01)

(52) U.S. Cl.

CPC ............ *A61C 7/002* (2013.01); *G16H 50/50* (2018.01); *A61C 7/08* (2013.01)

(58) Field of Classification Search

CPC ....... A61C 7/002; A61C 7/08; A61C 13/0004; G16H 50/50; G16H 50/70; G16H 50/20; G16H 20/30

See application file for complete search history.

(56) References Cited

U.S. PATENT DOCUMENTS 5,975,893 A 11/1999 Chishti et al.
6,227,850 B1 5/2001 Chishti et al.
(Continued)

FOREIGN PATENT DOCUMENTS

WO 2019213129 A1 11/2019

*Primary Examiner* — Robert A Sorey
*Assistant Examiner* — Kristine K Rapillo
(74) *Attorney, Agent, or Firm* — Shay Glenn LLP

(57) ABSTRACT

Methods and systems for processing dental workflows. In a pre-routing module, a determination may be made as to whether process(es) in generating an output workflow performed on a digital dental model should be manually or automatically based on comparing patient-specific clinical parameters against clinical rules. In a post-routing module, a determination may be made as to whether the output workflow contains output parameter value(s) that is outside of a range of acceptable output parameter values. An indicator to manually perform the process(es) may be transmitted if the post-routing module determines that output parameters value(s) is outside of the range of acceptable output parameter values. The output workflow may be modified based on the process(es) being manually or semi- manually performed. Dental appliance(s) may be fabricated in accordance with the modified output workflow.

21 Claims, 12 Drawing Sheets

(56) References Cited

U.S. PATENT DOCUMENTS 6,227,851 B1 5/2001 Chishti et al.
6,299,440 B1 10/2001 Phan et al.
6,318,994 B1 11/2001 Chishti et al.
6,371,761 B1 4/2002 Cheang et al.
6,386,878 B1 5/2002 Pavlovskaia et al.
6,406,292 B1 6/2002 Chishti et al.
6,409,504 B1 6/2002 Jones et al.
6,457,972 B1 10/2002 Chishti et al.
6,488,499 B1 12/2002 Miller
6,514,074 B1 2/2003 Chishti et al.
6,554,611 B2 4/2003 Chishti et al.
6,582,229 B1 6/2003 Miller et al.
6,602,070 B2 8/2003 Miller et al.
6,621,491 B1 9/2003 Baumrind et al.
6,688,886 B2 2/2004 Hughes et al.
6,726,478 B1 4/2004 Isiderio et al.
6,729,876 B2 5/2004 Chishti et al.
6,739,869 B1 5/2004 Taub et al.
6,767,208 B2 7/2004 Kaza
6,783,360 B2 8/2004 Chishti
7,040,896 B2 5/2006 Pavlovskaia et al.
7,063,532 B1 6/2006 Jones et al.
7,074,038 B1 7/2006 Miller
7,074,039 B2 7/2006 Kopelman et al.
7,077,647 B2 7/2006 Choi et al.
7,108,508 B2 9/2006 Hedge et al.
7,134,874 B2 11/2006 Chishti et al.
7,156,661 B2 1/2007 Choi et al.
7,160,107 B2 1/2007 Kopelman et al.
7,241,142 B2 7/2007 Abolfathi et al.
7,293,988 B2 11/2007 Wen
7,309,230 B2 12/2007 Wen
7,357,634 B2 4/2008 Knopp
7,555,403 B2 6/2009 Kopelman et al.
7,637,740 B2 12/2009 Knopp
7,689,398 B2 3/2010 Cheng et al.
7,736,147 B2 6/2010 Kaza et al.
7,746,339 B2 6/2010 Matov et al.
7,844,356 B2 11/2010 Matov et al.
7,844,429 B2 11/2010 Matov et al.
7,865,259 B2 1/2011 Kuo et al.
7,878,804 B2 2/2011 Korytov et al.
7,880,751 B2 2/2011 Kuo et al.
7,904,308 B2 3/2011 Arnone et al.
7,930,189 B2 4/2011 Kuo
7,942,672 B2 5/2011 Kuo
7,970,627 B2 6/2011 Kuo et al.
7,970,628 B2 6/2011 Kuo et al.
8,038,444 B2 10/2011 Kitching et al.
8,044,954 B2 10/2011 Kitching et al.
8,075,306 B2 12/2011 Kitching et al.
8,092,215 B2 1/2012 Stone-Collonge et al.
8,099,268 B2 1/2012 Kitching et al.
8,108,189 B2 1/2012 Chelnokov et al.
8,126,726 B2 2/2012 Matov et al.
8,260,591 B2 9/2012 Kass et al.
8,275,180 B2 9/2012 Kuo
8,401,826 B2 3/2013 Cheng et al.
8,439,672 B2 5/2013 Matov et al.
8,562,338 B2 10/2013 Kitching et al.
8,591,225 B2 11/2013 Wu et al.
8,788,285 B2 7/2014 Kuo
8,843,381 B2 9/2014 Kuo et al.
8,874,452 B2 10/2014 Kuo
8,896,592 B2 11/2014 Boltunov et al.
8,930,219 B2 1/2015 Trosien et al.
9,037,439 B2 5/2015 Kuo et al.
9,060,829 B2 6/2015 Sterental et al.
9,125,709 B2 9/2015 Matty
9,211,166 B2 12/2015 Kuo et al.
9,220,580 B2 12/2015 Borovinskih et al.
9,364,296 B2 6/2016 Kuo
9,375,300 B2 6/2016 Matov et al.
9,414,897 B2 8/2016 Wu et al.
9,492,245 B2 11/2016 Sherwood et al.
9,642,678 B2 5/2017 Kuo
10,248,883 B2 4/2019 Borovinskih et al.
10,342,638 B2 7/2019 Kitching et al.
10,463,452 B2 11/2019 Matov et al.
10,595,966 B2 3/2020 Carrier, Jr. et al.
10,617,489 B2 4/2020 Grove et al.
10,722,328 B2 7/2020 Velazquez et al.
10,758,322 B2 9/2020 Pokotilov et al.
10,779,718 B2 9/2020 Meyer et al.
10,792,127 B2 10/2020 Kopelman et al.
10,828,130 B2 11/2020 Pokotilov et al.
10,835,349 B2 11/2020 Cramer et al.
10,973,611 B2 4/2021 Pokotilov et al.
10,996,813 B2 5/2021 Makarenkova et al.
10,997,727 B2 5/2021 Xue et al.
11,020,205 B2 6/2021 Li et al.
11,020,206 B2 6/2021 Shi et al.
11,026,766 B2 6/2021 Chekh et al.
11,033,359 B2 6/2021 Velazquez et al.
11,071,608 B2 7/2021 Derakhshan et al.
11,096,763 B2 8/2021 Akopov et al.
11,116,605 B2 9/2021 Nyukhtikov et al.
11,147,652 B2 10/2021 Mason et al.
11,151,753 B2 10/2021 Gao et al.
11,154,381 B2 10/2021 Roschin et al.
11,259,896 B2 3/2022 Matov et al.
11,357,598 B2 6/2022 Cramer
11,395,717 B2 7/2022 Yuryev et al.
11,426,260 B1 * 8/2022 Raslambekov ........ A61C 7/002
11,432,908 B2 9/2022 Kopelman et al.
11,464,604 B2 10/2022 Makarenkova et al.
11,478,334 B2 10/2022 Matov et al.
11,484,389 B2 11/2022 Sterental et al.
11,521,732 B2 12/2022 Levin et al.
11,534,272 B2 12/2022 Li et al.
11,553,988 B2 1/2023 Mednikov et al.
11,633,268 B2 4/2023 Moalem et al.
11,642,195 B2 5/2023 Gao et al.
11,651,494 B2 5/2023 Brown et al.
11,654,001 B2 5/2023 Roschin et al.
11,707,344 B2 7/2023 Roschin et al.
11,810,271 B2 11/2023 Shi et al.
11,850,111 B2 12/2023 Derakhshan et al.
12,412,648 B2 * 9/2025 Levin ..................... A61C 7/002
2003/0008259 A1 1/2003 Kuo et al.
2003/0143509 A1 7/2003 Kopelman et al.
2003/0207227 A1 11/2003 Abolfathi
2004/0137400 A1 7/2004 Chishti et al.
2004/0152036 A1 8/2004 Abolfathi
2004/0197728 A1 10/2004 Abolfathi et al.
2004/0259049 A1 12/2004 Kopelman et al.
2005/0182654 A1 8/2005 Abolfathi et al.
2005/0244791 A1 11/2005 Davis et al.
2006/0127836 A1 6/2006 Wen
2006/0127852 A1 6/2006 Wen
2006/0127854 A1 6/2006 Wen
2006/0275731 A1 12/2006 Wen et al.
2006/0275736 A1 12/2006 Wen et al.
2008/0306724 A1 12/2008 Kitching et al.
2010/0009308 A1 1/2010 Wen et al.
2010/0068672 A1 3/2010 Arjomand et al.
2010/0068676 A1 3/2010 Mason et al.
2010/0092907 A1 4/2010 Knopp
2010/0167243 A1 7/2010 Spiridonov et al.
2013/0204599 A1 8/2013 Matov et al.
2017/0273760 A1 9/2017 Morton et al.
2018/0280118 A1 10/2018 Cramer
2019/0328487 A1 10/2019 Levin et al.
2019/0328488 A1 10/2019 Levin et al.
2020/0155274 A1 5/2020 Pimenov et al.
2020/0297458 A1 9/2020 Roschin et al.
2020/0306011 A1 10/2020 Chekhonin et al.
2021/0134436 A1 5/2021 Meyer et al.
2023/0149127 A1 * 5/2023 Nikolskiy ............ G06V 10/778
433/24

* cited by examiner

700

Determining, in a pre-routing module, if each of one or more processes for generating a dental workflow (e.g., treatment planning for tooth alignment using a series of aligners, treatment planning for restorative, etc.) should be performed on a digital dental model of the patient's dentition either manually or automatically
701

For each process, automatically generating an output workflow (e.g., treatment plan) if the pre-routing module indicates that the process is appropriate for automatic performance (e.g., using an automated treatment planning module), otherwise indicating that the process should be manually performed
703

For all (or in some examples, a subset) of the processes determine, in a post-routing module if the output workflow contains one or more parameter values that is outside of a range of acceptable parameter values.
705

Finalize/forwarding the output workflow if the post-routing module indicates that the output workflow is acceptable, otherwise transmitting an indicator to manually perform the one or more processes if the post-routing module determines that one or more parameters values is outside of the acceptable range of parameter values
707

Optionally modify the output workflow using a workflow modification module
709

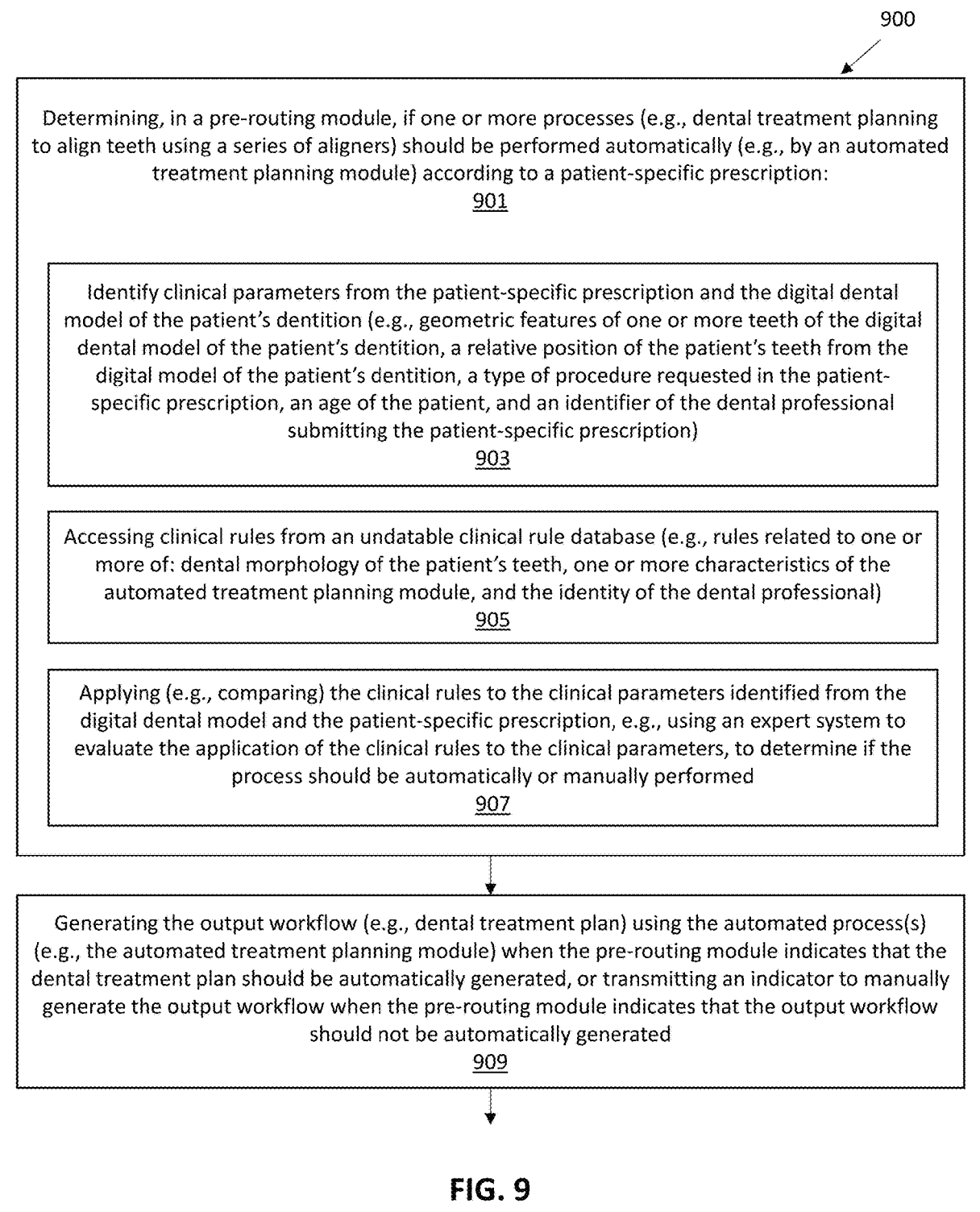

Determining, in a pre-routing module, if one or more processes (e.g., dental treatment planning to align teeth using a series of aligners) should be performed automatically (e.g., by an automated treatment planning module) according to a patient-specific prescription:
901

Identify clinical parameters from the patient-specific prescription and the digital dental model of the patient's dentition (e.g., geometric features of one or more teeth of the digital dental model of the patient's dentition, a relative position of the patient's teeth from the digital model of the patient's dentition, a type of procedure requested in the patient-specific prescription, an age of the patient, and an identifier of the dental professional submitting the patient-specific prescription)
903

Accessing clinical rules from an undatable clinical rule database (e.g., rules related to one or more of: dental morphology of the patient's teeth, one or more characteristics of the automated treatment planning module, and the identity of the dental professional)
905

Applying (e.g., comparing) the clinical rules to the clinical parameters identified from the digital dental model and the patient-specific prescription, e.g., using an expert system to evaluate the application of the clinical rules to the clinical parameters, to determine if the process should be automatically or manually performed
907

Generating the output workflow (e.g., dental treatment plan) using the automated process(s) (e.g., the automated treatment planning module) when the pre-routing module indicates that the dental treatment plan should be automatically generated, or transmitting an indicator to manually generate the output workflow when the pre-routing module indicates that the output workflow should not be automatically generated
909

FIG. 9

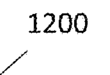

Receive an automatically-generated workflow (e.g., dental treatment planning to align teeth using a series of aligners, etc.) that was generated by an automated treatment planning module) according to a patient-specific prescription.
1201

Determine, in a post-routing module, if the workflow contains one or more values that is/are outside of a range of acceptable parameter values
1203

Identify parameters (e.g., tooth movement parameters )from the workflow
1205

Compare the parameters to a set of acceptable parameter values (retrieve the acceptable parameter values from a datastore of acceptable values)
1207

If any of the parameters are outside of the range of acceptable vales, determine (with a false-positive verification module) if these parameters are intended to be exceptions based on the prescriber's intent
1209

Review the human-readable (natural language, e.g., prescriber-written) prescription text using a trained machine-learning agent to identify exceptions for any of the parameter's outside of the range of acceptable values in the prescriber's instructions
1211

Output an indicator that the workflow (e.g., treatment plan) should be redone manually or with manual assistance if (1) there are one or more parameters outside of the range of acceptable values and (2) the one or more parameters are not exceptions based on the prescriber's written instructions
1213

FIG. 12

METHODS AND APPARATUSES FOR TREATMENT QUALITY ASSESSMENT

CLAIM OF PRIORITY

This patent application claims priority to U.S. Provisional Patent Application No. 63/412,871, titled "METHODS AND APPARATUSES FOR TREATMENT QUALITY ASSESSMENT," filed on Oct. 3, 2022 and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Treatment planning may be used in any medical procedure to help guide a desired outcome. For example, treatment planning may be used in orthodontic and dental treatments for orchestrating dental treatments to align teeth, e.g., using a series of patient-removable appliances (e.g., orthodontic aligners, palatal expanders, etc.), for applying a dental restorative (e.g., veneer, cap, bridge, etc.), or the like. Treatment planning may be performed in conjunction with the dental professional (e.g., dentist, orthodontist, dental technician, etc.), by generating a number of intermediate stages (steps) that may be sequentially performed to complete the treatment. This process may be interactive, adjusting the staging and in some cases the final target position, based on constraints on the movement of the teeth and the dental professional's preferences.

Automatic methods and systems for generating treatment plans have been proposed. However, in practice not all cases are well suited for automatic treatment planning. Unfortunately, in practice it may be extremely difficult and time consuming to determine which cases are well suited and which cases are not. Existing methods and apparatuses for automatically generating treatment plans may occasionally result in poor quality treatment, and such methods and apparatuses are ill-suited to detect these cases. What is needed is method and apparatuses that may address these problems.

SUMMARY OF THE DISCLOSURE

Described herein are methods and apparatuses (e.g., devices and systems, including software, firmware and/or hardware) for assisting or streamlining in workflows for generating treatment plans that may provide either pre-routing oversight before an automatic treatment planning module is used to generate a treatment plan and/or post-routing oversight after an automatic treatment planning module has generated the treatment plan, but before the treatment plan is passed onto to the prescribing dental professional (e.g., doctor, dentist, orthodontist, etc.).

In general, these methods and apparatuses may be used as part of, or as adjunctive to, an automatic treatment planning apparatus or method. For example, International patent application, PCTUS2019029990, titled "SYSTEMS AND METHODS OF MANAGING CUSTOMIZED RUN DISPLAY ELEMENTS WITH TREATMENT TEMPLATES BASED ON TREATMENT DOMAIN-SPECIFIC PROTOCOLS," filed on Apr. 30, 2019, and related U.S. patent application Ser. No. 16/399,834, filed Apr. 30, 2019, U.S. patent application Ser. No. 16/399,847 filed Apr. 30, 2019, U.S. patent application Ser. No. 16/399,852 filed Apr. 30, 2019, all describe apparatuses and methods (and automated treatment planning modules) for automatically generating treatment plans for aligning a patient's teeth. Each of these applications is herein incorporated by reference in its entirety.

The methods and apparatuses may include pre-routing and/or post-routing modules that may streamline the workflow for generating one or more treatment plans. As used herein "routing" may refer to the automated processing of treatment plans that may take as input a model (e.g., a digital model) of the patient's dentition (upper and/or lower arches, including teeth and in some cases gingiva and/or palate), as well as a prescription for a treatment (or treatments) provided by the dental professional. The prescription may include written text with instructions and/or supplemental instructions. Pre-routing typically refers to steps that may be performed before the input (e.g., digital dental model of the patient's teeth and the prescription for treating the patient's teeth) is passed on to one or more automated treatment planning stages (e.g., modules). Pre-routing may be advantageous in preventing the use of computing resources and time in situations where the resulting treatment plan(s) will be insufficient or otherwise undesirable. As mentioned above, it may be particularly difficult to know a priori which cases (e.g., which inputs) will result in poor quality treatment plans, particularly in cases where the dentition seems otherwise within normal morphologies. The pre-routing techniques described herein may determine if an automated treatment planning technique (e.g., module) is appropriate for a particular case, e.g., set of input and may either "pass" the proposed case or may issue and alert (flag, notification, etc.) and/or route the case for manual or semi-manual processing.

Post-routing typically refers to steps that may be performed after the input (e.g., digital dental model of the patient's teeth and the prescription for treating the patient's teeth) is passed on to one or more automated treatment planning stages (e.g., modules). Post routing may be advantageous in preventing transmitting of poor-quality treatment plan to the dental professional, which be also be time consuming and may erode trust in the automated process. A post-routing technique as described herein may determine if the automated treatment planning technique (e.g., module) using the input (prescription and digital dental model) provided a sufficient output (e.g., treatment plan). The post-routing techniques described herein may therefore "pass" the resulting treatment plan for further processing and/or for transmitting to the dental professional, or it may "fail" the treatment plan, triggering, alerting or notifying (e.g., issue an alert) that the case needs to be manually or semi-automatically revised. In some cases the failed treatment plan may be rejected completely, and a new treatment plan may be generated either manually or semi-automatically; in some cases the failed treatment plan may be modified.

Any of the methods and apparatuses described herein may include both pre-routing and post-routing techniques, or may include just pre-routing, or may include just post-routing. In general, these methods and apparatuses may be referred to herein as hybrid automated and manual routing techniques or dental workflows.

For example, described herein are methods and apparatuses that include both pre-routing and post-routing. These methods may help streamline automated or semi-automated workflows for generating treatment plans. For example, described herein are methods for processing a dental workflow for a dental treatment of a patient by a dental professional. These methods may include: determining, in a pre-routing module, if one or more processes should be performed on a digital dental model either manually or automatically; automatically performing any of the one or more processes on the digital dental model to generate an output workflow when the pre-routing module indicates that the process should be automatically performed; and determining in a post-routing module if the output workflow contains one or more parameter values that is outside of a range of parameter values; and transmitting an indicator to manually perform the one or more processes if the post-routing module determines that one or more parameters values is outside of the range of parameter values.

In any of these methods and apparatuses, the method may include determining, e.g., in a false-positive verification module, if the one or more parameter values that is outside of the range of parameter values is an exception based on an automatic review of a set of dental treatment instructions provided by the dental professional associated with the treatment instructions written in a natural language text; wherein transmitting the indicator to manually perform the one or more processes comprises transmitting the indictor only if the post-routing module determines that one or more parameters values that is outside of the range of parameter values and if the false-positive verification module does not identify an exception. The automatic review may comprise using a machine agent to identify an exception for the one or more parameter values from the natural language text of the set of dental treatment instructions. The false-positive verification module may be part of the post-routing module, or it may be separate (and in communication with) the post-routing module.

In any of these methods and apparatuses, determining in the pre-routing module if one or more processes (e.g., treatment planning to align teeth) should be performed on a digital dental model either manually or automatically may include determining based on the application of one or more clinical rules that are maintained in an updatable clinical rule database to the digital dental model. The one or more clinical rules may be related to one or more of: a dental morphology, a treatment to be performed on the patient's teeth represented by the digital dental model, one or more characteristics of the automated process, and an identifier of a dental professional associated with the treatment.

In any of these methods and apparatuses, the method may include generating and/or transmitting an indicator that the process (e.g., the treatment planning) should be manually performed. In cases where multiple processes are being reviewed, any of the one or more processes that the pre-routing module indicates should not be automatically performed may be separately indicated. In any of the methods and apparatuses described herein only a single process (e.g., treatment planning for aligning teeth) may be included.

The post-routing module may access a data set of acceptable parameters range values to determine if the one or more parameters values is outside of the range of parameter values.

For example, a method for processing a dental workflow for a dental treatment of a patient by a dental professional, may include: determining, in a pre-routing module, if one or more processes should be performed on a digital dental model either manually or automatically; automatically performing any of the one or more processes on the digital dental model to generate an output workflow when the pre-routing module indicates that the process should be automatically performed; determining in a post-routing module if the output workflow contains one or more parameters values that is outside of a range of parameter values; determining in a false-positive verification module if the one or more parameter values that is outside of the range of parameter values is an exception based on an automatic review of a set of dental treatment instructions provided by the dental professional associated with the treatment instructions written in a natural language text; and transmitting an indicator to manually perform the one or more processes if the post-routing module determines that one or more parameters values is outside of the range of parameter values and if the false-positive verification module does not identify an exception.

For example, described herein are methods for processing a dental workflow for a dental treatment of a patient by a dental professional, the method comprising: determining, in a pre-routing module, if one or more processes should be performed on a digital dental model either manually or automatically, based on the application of one or more clinical rules that are maintained in an updatable clinical rule database to the digital dental model, wherein the one or more clinical rules is related one or more of: a dental morphology, a treatment to be performed on the patient's teeth represented by the digital dental model, one or more characteristics of the automated process, and an identifier of a dental professional associated with the treatment; automatically performing any of the one or more processes on the digital dental model to generate an output workflow when the pre-routing module indicates that the process should be automatically performed; determining in a post-routing module if the output workflow contains one or more parameters values that is outside of a range of parameter values; and transmitting an indicator to manually perform the one or more processes if the post-routing module determines that one or more parameters values is outside of the range of parameter values.

Also described herein are apparatuses (e.g., systems, and/or software) for performing any of the methods described herein. For example a system may include: one or more processors; and a memory coupled to the one or more processors, the memory storing computer-program instructions, that, when executed by the one or more processors, perform a computer-implemented method comprising: determining, in a pre-routing module, if one or more processes should be performed on a digital dental model either manually or automatically; automatically performing any of the one or more processes on the digital dental model to generate an output workflow when the pre-routing module indicates that the process should be automatically performed; determining in a post-routing module if the output workflow contains one or more parameters values that is outside of a range of parameter values; and transmitting an indicator to manually perform the one or more processes if the post-routing module determines that one or more parameters values is outside of the range of parameter values.

In any of these systems, the computer-implemented method may further comprise determining in a false-positive verification module if the one or more parameter values that is outside of the range of parameter values is an exception based on an automatic review of a set of dental treatment instructions provided by a dental professional associated with the treatment instructions written in a natural language text; wherein transmitting the indicator to manually perform the one or more processes comprises transmitting the indictor only if the post-routing module determines that one or more parameters values that is outside of the range of parameter values and if the false-positive verification module does not identify an exception.

For example, the automatic review may include using a machine agent to identify an exception for the one or more parameter values from the natural language text of the set of dental treatment instructions.

In any of the methods and apparatuses described herein, the false-positive verification module may be part of the post-routing module. As mentioned above, determining, in the pre-routing module may comprise determining based on the application of one or more clinical rules that are maintained in an updatable clinical rule database to the digital dental model.

The one or more clinical rules may be related one or more of: a dental morphology, a treatment to be performed on the patient's teeth represented by the digital dental model, one or more characteristics of the automated process, and an identifier of a dental professional associated with the treatment.

Any of these systems may include transmitting an indicator to manually perform any of the one or more processes that the pre-routing module indicates should not be automatically performed. The post-routing module may access a data set of acceptable parameters set range values to determine if the one or more parameters values is outside of the range of parameter values.

For example, a system may include: one or more processors; a memory coupled to the one or more processors, the memory storing computer-program instructions, that, when executed by the one or more processors, perform a computer-implemented method comprising: determining, in a pre-routing module, if one or more processes should be performed on a digital dental model either manually or automatically; automatically performing any of the one or more processes on the digital dental model to generate an output workflow when the pre-routing module indicates that the process should be automatically performed; determining in a post-routing module if the output workflow contains one or more parameters values that is outside of a range of parameter values; determining in a false-positive verification module if the one or more parameter values that is outside of the range of parameter values is an exception based on an automatic review of a set of dental treatment instructions provided by a dental professional associated with the treatment instructions written in a natural language text; and transmitting an indicator to manually perform the one or more processes if the post-routing module determines that one or more parameters values is outside of the range of parameter values and if the false-positive verification module does not identify an exception.

In some examples a system may include: one or more processors; a memory coupled to the one or more processors, the memory storing computer-program instructions, that, when executed by the one or more processors, perform a computer-implemented method comprising: determining, in a pre-routing module, if one or more processes should be performed on a digital dental model of a patient's teeth either manually or automatically, based on the application of one or more clinical rules that are maintained in an updatable clinical rule database to the digital dental model, wherein the one or more clinical rules is related one or more of: a dental morphology, a treatment to be performed on the patient's teeth represented by the digital dental model, one or more characteristics of the automated process, and an identifier of a dental professional associated with the treatment; automatically performing any of the one or more processes on the digital dental model to generate an output workflow when the pre-routing module indicates that the process should be automatically performed; determining in a post-routing module if the output workflow contains one or more parameters values that is outside of a range of parameter values; and transmitting an indicator to manually perform the one or more processes if the post-routing module determines that one or more parameters values is outside of the range of parameter values.

Also described herein is software, e.g., a non-transitory computing device readable medium having instructions stored thereon that are executable by a processor to cause a computing device to perform any of the methods as described herein.

The methods and apparatuses (e.g., systems, devices, software, etc.) may include just a pre-routing module without a post-routing module as described herein. In general, the methods may be configured to perform a clinical routing of cases using an expert system. For example, a method for processing a workflow for a dental treatment of a patient when a dental professional submits a patient-specific prescription may include: determining, in a pre-routing module, if one or more processes should be performed on a digital dental model of the patient's dentition either manually or automatically, wherein the pre-routing module applies one or more clinical rules that are maintained in an updatable clinical rule database to the digital dental model and the patient-specific prescription, wherein the one or more clinical rules is related one or more of: a dental morphology of the patient's teeth, the patient-specific prescription, one or more characteristics of the automated process, and an identifier of the dental professional submitting the patient-specific prescription; and automatically performing any of the one or more processes on the digital dental model to generate an output workflow when the pre-routing module indicates that the process should be automatically performed, and transmitting an indicator to manually perform any of the one or more processes that the pre-routing module indicates should not be automatically performed.

In general, the dental treatment may be aligning the patient's teeth (e.g., orthodontic tooth movement). The one or more processes may comprise dental treatment planning, further wherein the output workflow comprises a dental treatment plan including a series of dental aligners. Any of these methods may include identifying, in the pre-routing module, clinical parameters from the patient-specific prescription and the digital dental model of the patient's dentition, wherein the pre-routing module applies the one or more clinical rules by comparing them to the clinical parameters. For example, the clinical parameters may include one or more of geometric features of one or more teeth of the digital dental model of the patient's dentition, a relative position of the patient's teeth from the digital dental model of the patient's dentition, a type of procedure requested in the patient-specific prescription, an age of the patient, and an identifier of the dental professional submitting the patient-specific prescription.

The pre-routing module may determine that the one or more processes should be manually or automatically performed using an expert-system evaluation of the one or more clinical rules. In some examples, the pre-routing module determines that the one or more processes should be manually or automatically performed by scoring each rule of the one or more clinical rules comparing the score to a threshold value. In some examples the pre-routing module determines that the one or more processes should be manually or automatically performed by indicating that the one or more processes should be manually performed when at least one of the one or more clinical rules indicates that the one or more processes should be manually performed.

In any of these methods and apparatuses, the one or more clinical rules may include one or more of: worn teeth, Bolton discrepancies, requirement for preserving interproximal space, the presence of primary teeth, the type of dentition, an orthognathic surgery, a centric relation/centric occlusion discrepancy, a scissor bite, an extraction, and excessive crowding. Thus, the clinical rules may set parameter for these features (e.g., no primary teeth or certain primary teeth, etc.).

Any of these methods and apparatuses may include updating the updatable clinical rule database. The updatable clinical rule database may be updated on an ongoing manner (e.g., dynamically).

As mentioned, also described herein are systems configured to perform these methods. For example, a system may include: one or more processors; a memory coupled to the one or more processors, the memory storing computer-program instructions, that, when executed by the one or more processors, perform a computer-implemented method comprising: determining, in a pre-routing module after a dental professional submits a patient-specific prescription for a patient, if one or more processes should be performed on a digital dental model of the patient's dentition either manually or automatically to generate an output workflow, wherein the pre-routing module applies one or more clinical rules that are maintained in an updatable clinical rule database to the digital dental model and the patient-specific prescription, wherein the one or more clinical rules is related to one or more of: a dental morphology of the patient's teeth, the patient-specific prescription, one or more characteristics of the automated process, and an identifier of the dental professional submitting the patient-specific prescription; and automatically performing any of the one or more processes on the digital dental model to generate the output workflow when the pre-routing module indicates that the process should be automatically performed, and transmitting an indicator to manually perform any of the one or more processes that the pre-routing module indicates should not be automatically performed.

As mentioned, the output workflow may comprise a dental treatment including aligning the patient's teeth using a series of dental aligners. The one or more processes may comprise dental treatment planning. The system may be configured to identify, in the pre-routing module, clinical parameters from the patient-specific prescription and the digital dental model of the patient's dentition, wherein the pre-routing module applies the one or more clinical rules by comparing them to the clinical parameters. The clinical parameters may comprise one or more of geometric features of one or more teeth of the digital dental model of the patient's dentition, a relative position of the patient's teeth from the digital dental model of the patient's dentition, a type of procedure requested in the patient-specific prescription, an age of the patient, and an identifier of the dental professional submitting the patient-specific prescription. The pre-routing module may determine that the one or more processes should be manually or automatically performed using an expert-system evaluation of the one or more clinical rules.

In some examples, the pre-routing module determines that the one or more processes should be manually or automatically performed by scoring each rule of the one or more clinical rules comparing the score to a threshold value. The pre-routing module may determine that the one or more processes should be manually or automatically performed by indicating that the one or more processes should be manually performed when at least one of the one or more clinical rules indicates that the one or more processes should be manually performed. The one or more clinical rules may include one or more of: worn teeth, Bolton discrepancies, requirement for preserving interproximal space, the presence of primary teeth, the type of dentition, an orthognathic surgery, a centric relation/centric occlusion discrepancy, a scissor bite, an extraction, and excessive crowding.

Also described herein are methods for processing a dental treatment plan for aligning a patient's teeth when a dental professional submits a patient-specific prescription for a series of dental aligners, the method comprising: determining, in a pre-routing module, if dental treatment planning should be performed by an automated treatment planning module according to the patient-specific prescription using a digital dental model of the patient's dentition, wherein the pre-routing module applies one or more clinical rules that are maintained in an updatable clinical rule database, further wherein the one or more clinical rules is related to one or more of: a dental morphology of the patient's teeth, one or more characteristics of the automated treatment planning module, and an identifier of the dental professional; and generating the dental treatment plan using the automated treatment planning module when the pre-routing module indicates that the dental treatment plan should be automatically generated, or transmitting an indicator to manually generate the dental treatment plan when the pre-routing module indicates that dental treatment plan should not be automatically generated.

The may include identifying, in the pre-routing module, clinical parameters from the patient-specific prescription and the digital dental model of the patient's dentition, wherein the pre-routing module applies the one or more clinical rules by comparing them to the clinical parameters. The clinical parameters may comprise one or more of geometric features of one or more teeth of the digital dental model of the patient's dentition, a relative position of the patient's teeth from the digital dental model of the patient's dentition, a type of procedure requested in the patient-specific prescription, an age of the patient, and an identifier of the dental professional submitting the patient-specific prescription.

The pre-routing module may determine that the dental treatment plan should be manually or automatically performed using an expert-system evaluation of the one or more clinical rules. The pre-routing module may determine that the dental treatment plan should be manually or automatically performed by scoring each rule of the one or more clinical rules comparing the score to a threshold value. The pre-routing module may determine that the dental treatment plan should be manually or automatically performed by indicating that the dental treatment plan should be manually performed when at least one of the one or more clinical rules indicates that the dental treatment planning should be manually performed. As mentioned, the one or more clinical rules may include one or more of: worn teeth, Bolton discrepancies, requirement for preserving interproximal space, the presence of primary teeth, the type of dentition, an orthognathic surgery, a centric relation/centric occlusion discrepancy, a scissor bite, an extraction, and excessive crowding.

Also described herein are systems comprising: one or more processors; a memory coupled to the one or more processors, the memory storing computer-program instructions, that, when executed by the one or more processors, perform a computer-implemented method comprising: determining, in a pre-routing module, if one or more processes should be performed on a digital dental model of the patient's dentition either manually or automatically, wherein the pre-routing module applies one or more clinical rules that are maintained in an updatable clinical rule database to the digital dental model and a patient-specific prescription, wherein the one or more clinical rules is related to one or more of: a dental morphology of the patient's teeth, the patient-specific prescription, one or more characteristics of the automated process, and an identifier of a dental professional submitting the patient-specific prescription; and automatically performing any of the one or more processes on the digital dental model to generate an output workflow when the pre-routing module indicates that the process should be automatically performed, and transmitting an indicator to manually perform any of the one or more processes that the pre-routing module indicates should not be automatically performed.

The methods and apparatuses described herein may also be configured to include post-processing routing but not pre-processing routing. Although post-processing may include an automated method of detecting that there is a problem with a workflow (e.g., treatment plan), the post-processing module (or an accessory module coupled to the post-processing module) may also eliminate false-positives from the process, at least in part by using the prescription, via, e.g., human readable text analysis for automatic quality assessment. For example, the methods and apparatuses described herein may examine the prescribing dental practitioner's instructions and comments for automatic treatment quality assessment (e.g., to determine if variations from the expected parameters for the treatment plan are, in fact, permitted). Thus, any of these apparatuses and methods may include an agent (e.g., a machine learning agent) configured to build and/or use a natural language processing model and semantic text analysis to detect the most frequently requested clinical parameters to determine if the prescription includes exceptions to the otherwise limits on the acceptable ranges of parameters.

For example, described herein are methods for processing a workflow for a dental treatment of a patient when a dental professional submits a patient-specific prescription, the method comprising: receiving an output workflow that was automatically generated by performing one or more processes on a digital dental model based on the patient-specific prescription; determining in a post-routing module if the output workflow contains one or more parameters having a value that is outside of a range of acceptable parameter values, wherein the post-routing module accesses a database of acceptable parameter values; determining in a false-positive verification module if the one or more parameter values that is outside of the range of acceptable parameter values is an exception based on an review by a machine agent of the patient-specific prescription, wherein the patient-specific prescription comprises a set of dental treatment instructions in a natural language text, wherein the machine agent identifies the exception for the one or more parameter values from the natural language text of the patient-specific prescription; and transmitting an indicator to manually perform the one or more processes if the post-routing module determined that one or more parameter values was outside of the range of acceptable parameter values and if the false-positive verification module did not determine that the one or more parameter values that was outside of the range of acceptable parameter values was an exception.

In general, the false-positive verification module may be part of the post-routing module, or it may be separate from the post-routing module.

The output workflow may refer to a dental treatment plan, and in particular a dental treatment plan having a series of dental aligners. The dental treatment may include aligning the patient's teeth and the one or more processes comprises dental treatment planning. In any of these methods and apparatuses automatically performing one or more processes may include dental treatment planning in a treatment planning module, further wherein the output workflow comprises a dental treatment plan including a series of dental aligners.

The post-routing module may be configured to determine if the output workflow contains one or more parameters values that is outside of the range of acceptable parameter values for one or more of: overbite, overjet, attachments, staging, filing position of a tooth, occlusion, rotation of a tooth, anterior leveling, and torque. The machine agent may comprise a machine learning agent trained to identify one or more exceptions from the set of dental treatment instructions in the natural language text. In any of these methods and apparatuses, transmitting an indicator may comprise transmitting the patient-specific prescription to a technician for review and revision.

Also described herein are methods for processing a dental treatment plan for aligning a patient's teeth when a dental professional submits a patient-specific prescription for a series of dental aligners, the method comprising: generating a dental treatment plan from an automated treatment planning module using a digital dental model of the patient's dentition and the patient-specific prescription; determining in a post-routing module if the dental treatment plan contains one or more parameters having a value that is outside of a range of acceptable parameter values, wherein the post-routing module accesses a database of acceptable parameter values; determining in a false-positive verification module if the one or more parameter values that is outside of the range of acceptable parameter values is an exception based on an review of the patient-specific prescription by a machine agent, wherein the patient-specific prescription comprises a set of dental treatment instructions in a natural language text, and wherein the machine agent identifies the exception for the one or more parameter values from the natural language text of the patient-specific prescription; and transmitting an indicator to manually generate the dental treatment plan if the post-routing module determined that one or more parameter values was outside of the range of acceptable parameter values and if the false-positive verification module did not determine that the one or more parameter values that was outside of the range of acceptable parameter values was an exception.

A system for processing a dental treatment plan for aligning a patient's teeth may include: one or more processors; a memory coupled to the one or more processors, the memory storing computer-program instructions, that, when executed by the one or more processors, perform a computer-implemented method comprising: generating an output workflow for a dental treatment of a patient when a dental professional submits a patient-specific prescription by automatically performing one or more processes on a digital dental model based on the patient-specific prescription; determining in a post-routing module if the output workflow contains one or more parameters having a value that is outside of a range of acceptable parameter values, wherein the post-routing module accesses a database of acceptable parameter values; determining in a false-positive verification module if the one or more parameter values that is outside of the range of acceptable parameter values is an exception based on an review by a machine agent of the patient-specific prescription, wherein the patient-specific prescription comprises a set of dental treatment instructions in a natural language text, wherein the machine agent identifies the exception for the one or more parameter values from the natural language text of the patient-specific prescription; and transmitting an indicator to manually perform the one or more processes if the post-routing module determined that one or more parameter values was outside of the range of acceptable parameter values and if the false-positive verification module did not determine that the one or more parameter values that was outside of the range of acceptable parameter values was an exception.

In any of these systems, the false-positive verification module may be part of the post-routing module, or it may be separate. The output workflow may include a dental treatment plan including a series of dental aligners. The dental treatment may comprise aligning the patient's teeth and the one or more processes comprises dental treatment planning. Automatically performing one or more processes may comprise dental treatment planning in a treatment planning module, further the output workflow may comprise a dental treatment plan including a series of dental aligners. The post-routing module may be configured to determine if the output workflow contains one or more parameters values that is outside of the range of acceptable parameter values for one or more of: overbite, overjet, attachments, staging, filing position of a tooth, occlusion, rotation of a tooth, anterior leveling, and torque. The machine agent may comprise a machine learning agent trained to identify one or more exceptions from the set of dental treatment instructions in the natural language text. Transmitting an indicator may comprise transmitting the patient-specific prescription to a technician for review and revision.

A system may include: one or more processors; and a memory coupled to the one or more processors, the memory storing computer-program instructions, that, when executed by the one or more processors, perform a computer-implemented method comprising: generating a dental treatment plan for aligning a patient's teeth from an automated treatment planning module using a digital dental model of the patient's dentition and a patient-specific prescription when a dental professional submits the patient-specific prescription for a series of dental aligners; determining in a post-routing module if the treatment plan contains one or more parameters having a value that is outside of a range of acceptable parameter values, wherein the post-routing module accesses a database of acceptable parameter values; determining in a false-positive verification module if the one or more parameter values that is outside of the range of acceptable parameter values is an exception based on an review of the patient-specific prescription by a machine agent, wherein the patient-specific prescription comprises a set of dental treatment instructions in a natural language text, and wherein the machine agent identifies the exception for the one or more parameter values from the natural language text of the patient-specific prescription; and transmitting an indicator to manually generate the dental treatment plan if the post-routing module determined that one or more parameter values was outside of the range of acceptable parameter values and if the false-positive verification module did not determine that the one or more parameter values that was outside of the range of acceptable parameter values was an exception.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 7 illustrates one example of a method for processing a dental workflow including both pre-routing and post-routing modules as described herein.

FIG. 9 illustrates an example of a method of processing a dental workflow including a pre-routing module.

FIG. 12 illustrates an example of a method of processing a dental workflow including a post-routing module.

DETAILED DESCRIPTION

Figure 1A:
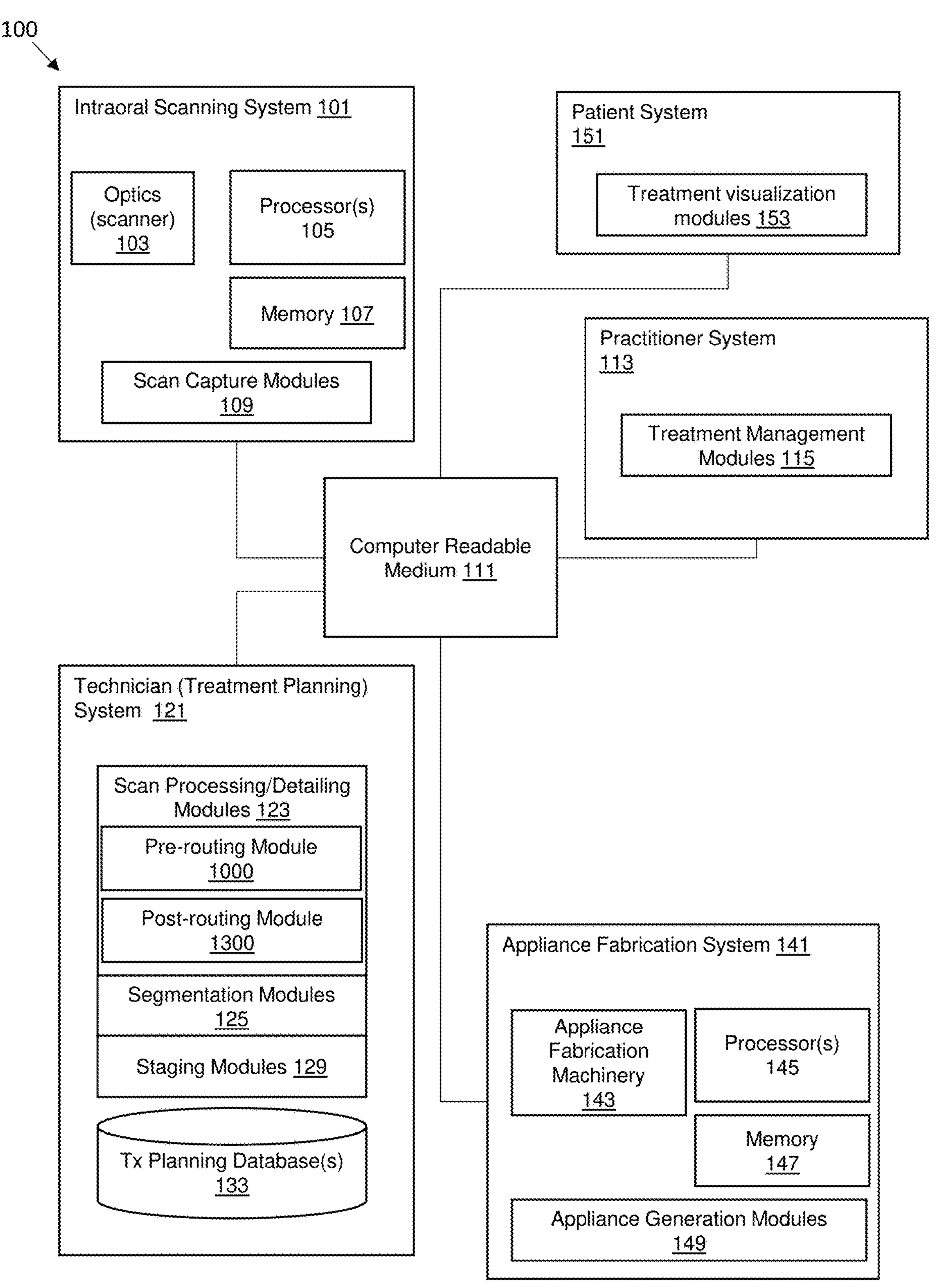
FIG. 1A schematically illustrates an example of a dental computing environment for implementing the methods and apparatuses described herein.

Described herein are methods and apparatuses (e.g., system, including software) for processing dental workflows. In particular, described herein are methods and apparatuses for processing dental treatment plan for aligning a patient's teeth when a dental professional submits a patient-specific prescription for a series of dental aligners. The workflow may be dental treatment plans, and these methods and apparatuses may be used to provide efficient hybrid automatic/manual routing for the workflows. In some examples the workflow incudes a pre-routing module that may determine if an automatic or automated process (e.g., for generating a dental treatment plan) is appropriate for a given set of inputs; the inputs may be a digital model of the patient's dentition, as well as a prescription, e.g., a prescription for a series of dental appliances to be used to effect the treatment. Any of these methods and apparatuses may also or alternatively include a post-routing module that is configured to determine if an automatic or automated process (e.g., for generating a dental treatment plan) is appropriate for the inputs (e.g., the digital model of the patient's dentition and the prescription), even when there may be exceptions to the rules indicating that the resulting workflow has one or more parameters outside of the normally allowable ranges.

For example, a workflow having a hybrid automated/manual routing may be useful in treatment planning to straighten a patient's teeth, and/or to apply a dental restorative (e.g., veneer, cap, bridge, etc.). The current state of the art in dental treatment planning or dental workflows (e.g. ortho, restorative, etc.) may require significant human involvement. Increasingly, this planning can be automated through the use of algorithmic or AI/Machine Learning techniques. However, it may still be useful or necessary to provide a combination of automated and human processes. As described herein an otherwise fully manual process can be converted to a hybrid process (that may later be easily converted to a fully automated process) through the decomposition of the process into steps or modules, including in particular the use of pre-routing and/or post-routing modules to ensure a minimum of human involvement while maintaining quality. The methods and apparatuses described herein may allow for a stable and reliable approach to migrating from a fully manual workflow to a fully automated workflow. In practice, the hybrid workflows described herein may allow for the use of an automated workflow to the extent possible in the current state of automation. These method and apparatuses may also allow for a methodical approach to considering automation in a given environment. Any of these methods and apparatuses may further allow for multiple automated approaches to be used, based on a pre-process routing determination and/or a simultaneous run of multiple automation systems with voting or result-combination.

The methods and apparatuses (e.g., systems, software, etc.) described herein address a longstanding and pernicious problem in dental and orthodontic care, and in particular, problems associated with the use of digital dental models and treatment planning, in which a dental professional transmit instructions and patient information to an (often remote) processing site that is tasked with generating proposed treatment planning steps under the guidance of the dental professional in an accurate and efficient manner. Traditionally even when assisted by software, this process has required a lot of manual intervention, which results in much longer delays in treatment time, increased cost and effort. Although it has been expected that a certain amount of manual effort is needed, determining when this manual effort is needed, particularly early in the procedure, has proven exceptionally difficult to determine. The methods and apparatuses described herein may, for the first time, provide the tools needed to minimize the amount of manual intervention in the treatment planning process to just those periods that are necessary. This may be done by applying pre- and post-routing modules that are configured to control the workflow, including when manual intervention is needed.

For example, doctors typically express their preferences for particular finishing instructions during dental (and/or orthodontic) treatment in special instructions, e.g., special instructions for upper and lower jaws. These preferences/instructions may require routing to technicians for manual interpretation requiring that the technician spend time reviewing the instructions, often before realizing that no action needs to be taken. Existing recommendation and classification systems typically cannot ensure the absence of false negative assumptions. The methods and apparatuses described herein may automatically predict instruction types with minimal false non-meaningful decisions and may therefore minimize the number of manual steps in a manner that has not previously been possible, minimizing the need for manual re-checking of assumed prediction and text instructions from the dental professional. This has proven to provide a significant cost and time savings. The methods described herein include pre-routing and post-routing modules, as well as verification modules, that divide up manual and automatic analysis based on an analysis of the dental professional's text instructions, and may use a trained neural network (e.g., applying machine learning algorithms) to analyze available text samples.

In some examples these methods and apparatuses may include a pre-routing module, one or more automated processes, and a post-routing module. Any manual step in a workflow may be augmented by one or more of these components. In general, the workflow may be a treatment plan, and the one or more automated processes may be configured to design, build and/or generate the treatment plan. In some examples the treatment plan is a treatment plan for moving or aligning the patient's teeth.

As illustrated in FIG. 1, the methods and apparatuses described herein may be used at or with one or more parts of a dental computing environment that includes a technician system 121, a practitioner (dental professional) system 113, a patient system 151, one or more scanners 101, and a fabrication system 141. In particular, these methods and apparatuses may be used as part of the technician system 121, for example, to quickly and efficiently generate an accurate digital model of the patient's dentition, a treatment plans, and/or designs for one or more dental appliances to perform the treatment plan. For example, FIG. 1 schematically illustrates one variation of a dental computing environment 100 that may generate one or more orthodontic treatment plans specific to a patient based on the instructions of the dental professional (practitioner), and may fabricate dental appliances that accomplish the treatment plan to treat a patient, under the direction of the dental professional. In the example computing environment 100 shown in FIG. 1 each of the systems shown may communicate directly or indirectly with each other; for example, the intraoral scanning system 101, doctor system 113, technician (treatment planning) system 121, patient system 151, and appliance fabrication system 141 may communicate directly or indirectly with each other including through a computer-readable medium 111 (each of these systems may include computer-readable media which may be shared or separate). In some variations a computing environment (dental computing system) 100 may include just one or a subset of these systems (which may also be referred to as sub-systems of the overall system 100). Further, one or more of these systems may be combined or integrated with one or more of the other systems (sub-systems), such as, e.g., the patient system and the doctor system may be part of a remote server accessible by doctor and/or patient interfaces. The computer readable medium 111 may divided between all or some of the systems (subsystems); for example, the technician (treatment planning) system and appliance fabrication system may be part of the same sub-system and may be on a computer readable medium 111. Further, each of these systems may be further divided into sub-systems or components that may be physically distributed (e.g., between local and remote processors, etc.) or may be integrated.

As shown in FIG. 1A, the technician system 121 may communicate with the practitioner system and may receive from the practitioner system and/or the intraoral scanning system the scans and/or models of the patient's teeth, as well as practitioner instructions for treatment, and may oversee the generation of the treatment plan base on these inputs. As will be described in greater detail below, the technician system 121 may include one or both of the pre-routing module 1000 and post-routing module 1300, which may be part of the scan process/detailing module(s) 123 or may be separate from these. These modules may be part of the digital detailing of the treatment plan and/or dental models of the patient's teeth. The technician (e.g., treatment planning) system 121 may therefore include any of the methods and apparatuses described herein, and/or may output or input to other systems, including the practitioner system 113. As mentioned, the technician (e.g., treatment planning) system 121 may include scan processing/detailing modules 123, segmentation modules 125, staging modules 129, and additional modules and databases, including treatment planning database(s) 133. In general, the technician (e.g., treatment planning) system 121 can determine a treatment plan for any feasible patient. The scan processing/detailing modules 123 can receive or obtain dental scans (such as scans from the intraoral scanning system 101) and can process the scans to "clean" them by removing scan errors and, in some cases, enhancing details of the scanned image.

The technician (e.g., treatment planning) system 121 may include a segmentation system or it may access a segmentation system and/or may include any of the engines (e.g., scan segmentation engine(s), 3D fusion engine(s), tooth modeling engine(s), tooth labeling engine(s), and/or 2D alignment engine). A technician (e.g., treatment planning) system 121 may include a segmentation modules 125 that can segment a dental model into separate parts including separate teeth, gums, jaw bones, and the like. In some cases, the dental models may be based on scan data from the scan processing/detailing modules 123.

The staging modules 129 may determine different stages of a treatment plan. Each stage may correspond to a different dental aligner. The staging modules 129 may also determine the final position of the patient's teeth, in accordance with a treatment plan. Thus, the staging modules 129 can determine some or all of a patient's orthodontic treatment plan. In some examples, the staging modules 129 can simulate movement of a patient's teeth in accordance with the different stages of the patient's treatment plan.

An intraoral scanning system 101 may include an intraoral scanner as well as one or more processors for processing images. For example, an intraoral scanning system 101 can include optics (e.g., len(es), light sources, etc. 103, processor(s) 105, a memory 107, scan capture modules 109, etc. In general, the intraoral scanning system 101 can capture one or more images of a patient's dentition. Use of the intraoral scanning system 101 may be in a clinical setting (doctor's office or the like) or in a patient-selected setting (the patient's home, for example). In some cases, operations of the intraoral scanning system 101 may be performed by an intraoral scanner, dental camera, cell phone or any other feasible device.

The intraoral scanning system 101 can provide images of the patient's dentition to the technician system 121 and/or a clinician through the practitioner system 113. The images may be captured through the intraoral scanning system and may also include images of a simulation of tooth movement based on a treatment plan from the technician system 121.

In some examples, the treatment management modules 115 can enable the doctor to modify or revise a treatment plan, particularly when images and/or output provided by the technician system 121 indicate that the movement of the patient's teeth may not be as intended or requested by the dental practitioner. The pre- and post-routing modules may also coordinate communication between the technician (e.g., treatment planning) system 121 and the practitioner system 113, as described in detail below. The practitioner system 113 may include one or more processors configured to execute any feasible non-transitory computer-readable instructions to perform any feasible operations described herein.

The patient system 151 can include treatment visualization modules 153. In general, the patient system 151 can provide a "patient facing" interface to the computing environment 100. The treatment visualization modules 153 can enable the patient to visualize how a orthodontic treatment plan has progressed and also visualize a predicted outcome (e.g., a final position of teeth).

The appliance fabrication system 141 can include appliance fabrication machinery 143, processor(s) 145, memory 147, and appliance generation modules 149. In general, the appliance fabrication system 141 can directly or indirectly fabricate aligners to implement an orthodontic treatment plan. In some examples, the orthodontic treatment plan may be stored in the treatment planning database(s) 149. In general, the treatment plan determined by the technician system 121 may be used to generate one or more dental appliances by outputting one or more digital files including fabrication instructions and/or parameters for all or some of the dental appliances corresponding to the treatment plan. The file may be read by the appliance fabrication system 141, including by the appliance fabrication machinery 143.

The appliance fabrication machinery 143 may include any feasible implement or apparatus that can fabricate any suitable dental aligner. The appliance generation modules 149 may include any non-transitory computer-readable instructions that, when executed by the processor(s) 145, can direct the appliance fabrication machinery 143 to produce one or more dental aligners. The memory 147 may store data or instructions for use by the processor(s) 145. In some examples, the memory 147 may temporarily store a treatment plan, dental models, or intraoral scans.

The computer-readable medium 111 may include some or all of the elements described herein with respect to the computing environment 100. The computer-readable medium 111 may include non-transitory computer-readable instructions that, when executed by a processor, can provide the functionality of any device, machine, or module described herein.

Figure 1B:
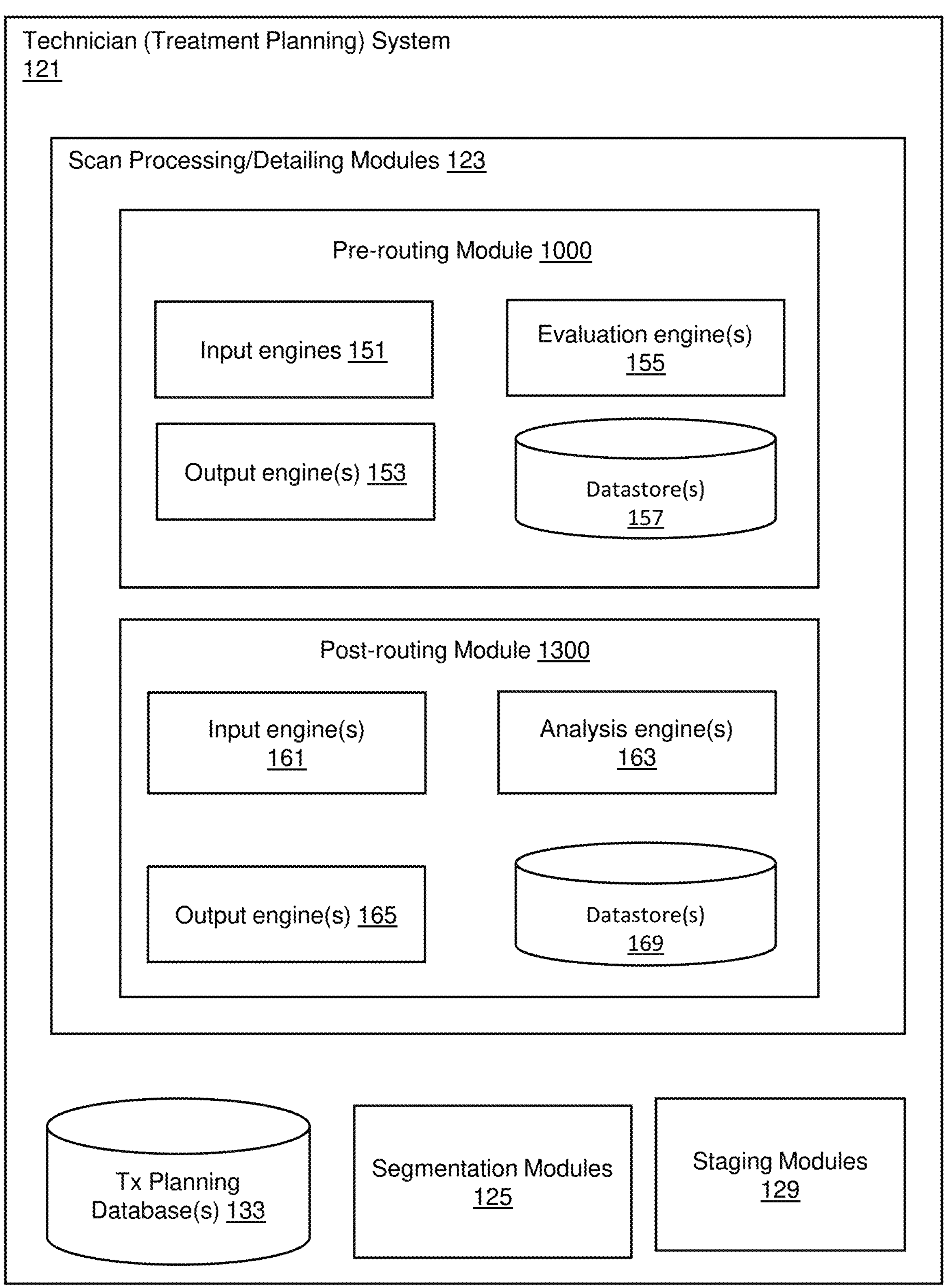
FIG. 1B schematically illustrates an example of a technician (treatment planning) system.

FIG. 1B is a block diagram of one example of a technician system 121. The technician system 121 may include a pre-routing module 1000 and a post-routing module 1300 that may be part of the scan processing/detailing module 123. In general, the pre-routing module 1000 (described in greater detail in FIG. 10, below) may include one or more input engines 151, e.g., a digital dental module input engine, process input engine, etc., one or more evaluation engines 155 (e.g., clinical rules evaluation engine, clinical rules update engines, etc.) and one or more output engines 153. The pre-routing module 1000 may also include one or more data stores 157, including clinical rules data stores. The post-routing engine 1300 (described in greater detail in reference to FIG. 13, below) may include one or more input engines 161, e.g., a prescription input engine, digital dental model input engine, workflow input engine, etc., one or more analysis engines 163 (e.g., false-positive verification module, treatment comparison module, workflow parsing module, etc.) and one or more output engines 165. The pre-routing module 1000 may also include one or more data stores 169, including acceptable parameter data stores. In general, the scan detailing modules, including the pre-routing module and post-routing module, may be part of a workflow for preparing a dental treatment plan, and ultimately, providing one or more dental appliance to perform the treatment plan. As mentioned, these methods and systems may be control and optimize what is performed automatically versus what requires manual intervention.

Figures 2, 3:
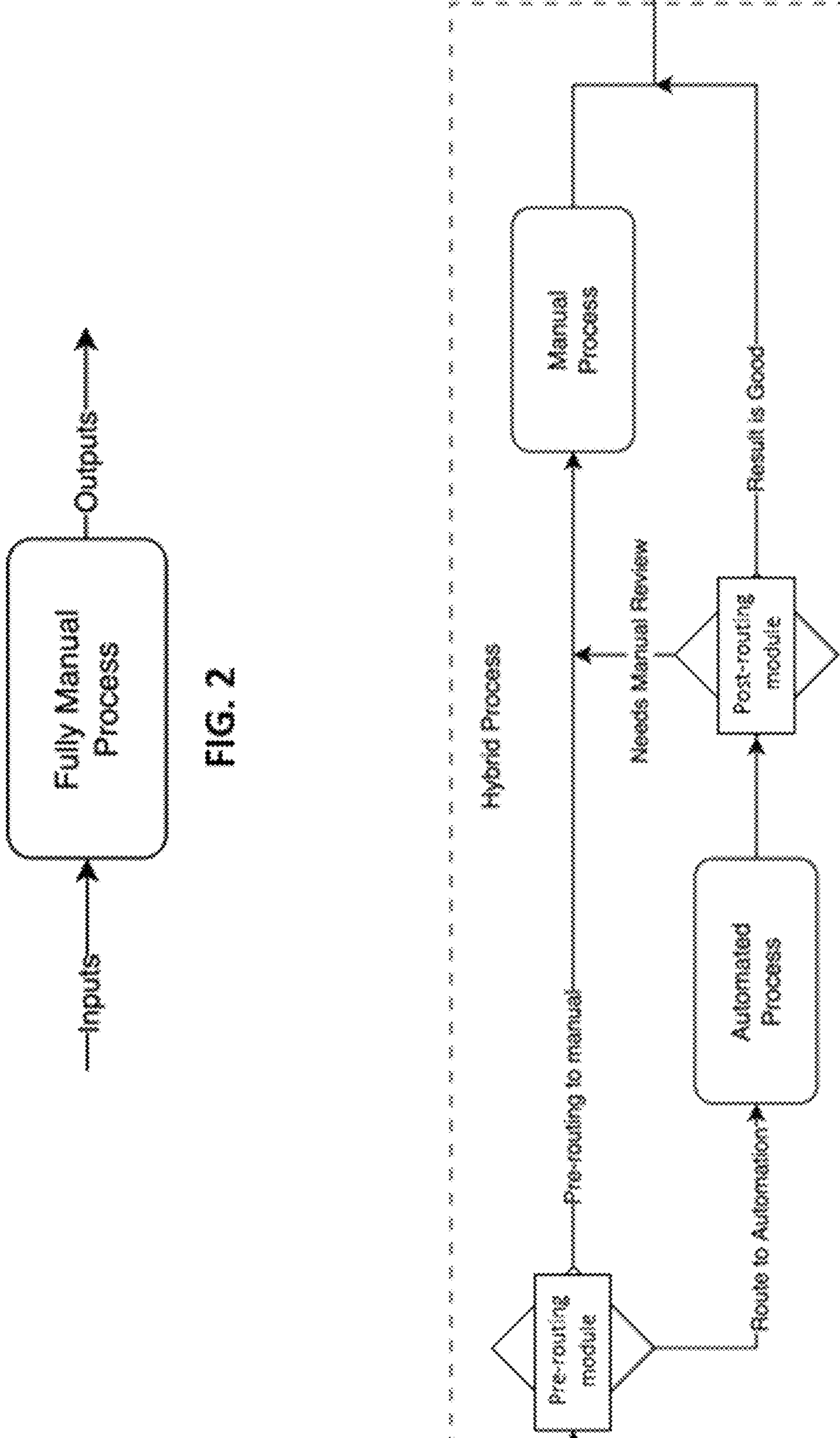
FIG. 2 schematically illustrates one example of a workflow.
FIG. 3 schematically illustrates an example of a hybrid automated/manual workflow (e.g., for a dental process) including both a pre-routing module and a post-routing module.

For example, a workflow comprising one or more manual processes is illustrated in FIG. 2. In this process, inputs arrive to the system and are processed by a person, potentially with some form of automated support. The process is limited by the number and speed of the persons involved in the process. FIG. 2 illustrates a single manual process in a workflow. The manual process of FIG. 2 can be replaced by a hybrid automation process such as that shown schematically in FIG. 3. In this hybrid process, the original manual process is augmented with a series of components, including: a pre-routing module, e.g., an optional component that determines (automatically) if the inputs are suitable for the automation process. If the inputs are suitable for automation (e.g., for automated treatment planning), then the inputs are routed to the automated process. In the case of dental treatment planning, the pre-routing module can make use of a variety of dental characteristics or clinical conditions plus knowledge of the strengths and weaknesses of the automated process in order to route to the manual or automated process.

The pre-routing module may, if it deems the automated process to be appropriate given the specific inputs, pass the inputs on to the automated process to automatically produce the desired output that would have otherwise need to have been generated by the technician. The automated process may be specific to the workflow under consideration. For example, the automated process may include RTM, DDT, segmentation, final position calculation, parsing doctor feedback for a revised final position, etc. The automated process may collectively determine treatment planning, e.g., based on the input of the patient's dentition (via a digital dental model of the patient's dentition) and the prescription for treatment. After the automated process is performed, the result may optionally be passed to a post-routing module.

Post-process routing may evaluate the automated result and determines if it is of sufficient quality to be passed on to the next step in the workflow or if it should be sent to the manual process for review and/or complete revision. In particular, as will be described in greater detail below, a post-routing module may compare parameters of the automatically determined treatment plan to a set of acceptable parameter values but may also check with the prescription (including in particular, checking for natural language writings in the prescription) to determine exceptions to these parameters that may be specific to a case of to the dental practitioner prescribing the procedure.

For example, FIG. 3 illustrate the basic hybrid process model described above. The pre-routing module and the post-routing module may be optional. For example, if there is no pre-routing module then the inputs may always be sent to the automated process. If the method or apparatus does not include a post-routing module, then the result of the automation step may always be passed on to the next step in the workflow. If neither the pre-module routing nor the post-process routing are in place, then the process is fully automated, and any manual processes are bypassed completely.

Figures 4, 5:
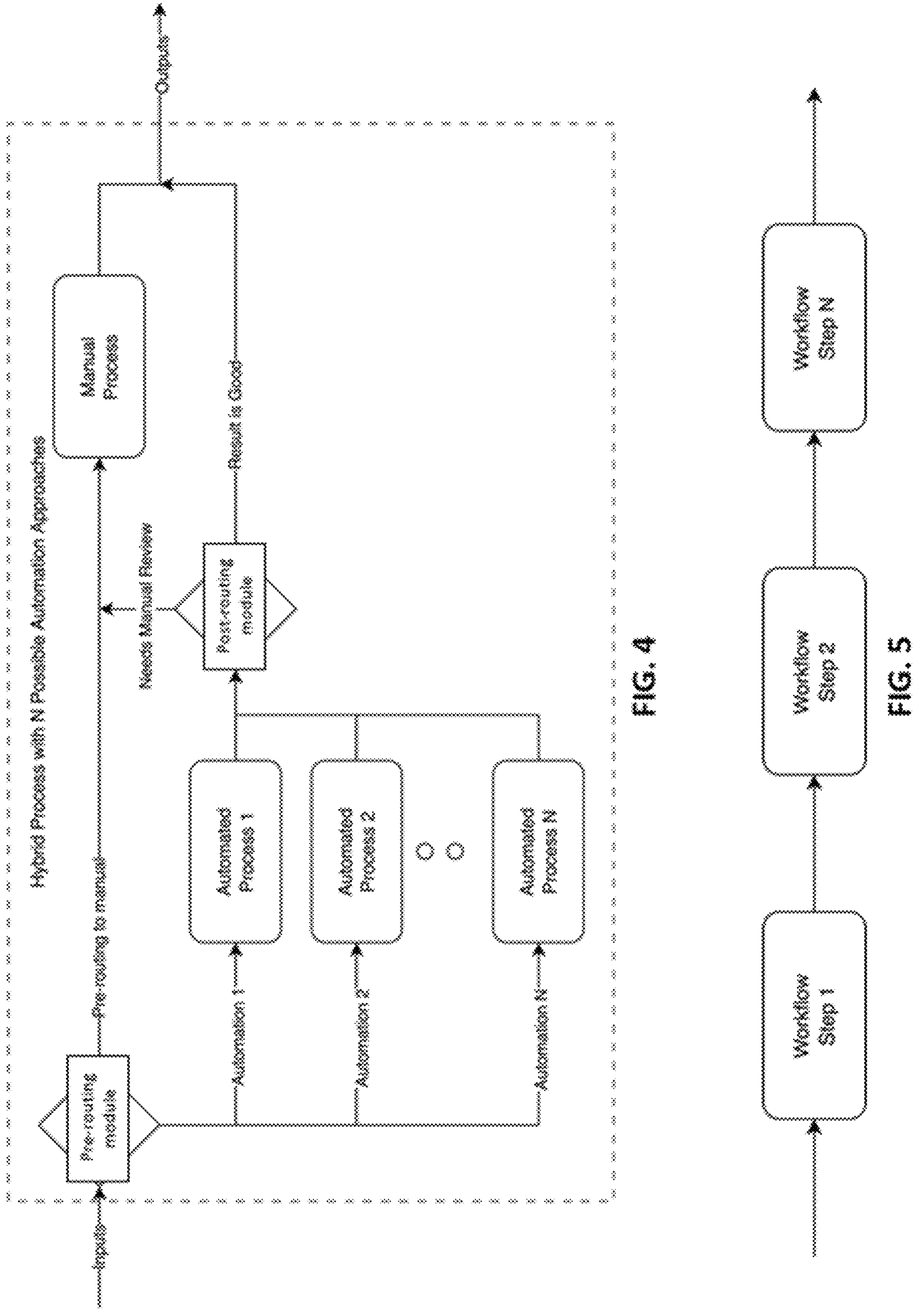
FIG. 4 schematically illustrates an example of a hybrid automated/manual workflow including a plurality of (n) different processes in parallel.
FIG. 5 schematically illustrates an example of a workflow having multiple sequential steps (e.g. processes).

In some contexts, more than one automated process may exist for a single manual process. Examples of this may include: multiple independent approaches to automating the same manual process (e.g., multiple independent approaches to segment a dental mesh or to identify and remove braces from a mesh); and multiple specialized automation approaches, each of which is designed for a set of input parameters (e.g., having a different mesh segmentation model for full arch scans vs partial arch scans as seen in restorative dentistry). In these cases, hybrid processing approach of FIG. 3 can be augmented as seen in FIG. 4. Depending on the use case, the pre-routing module and the post-routing module may have additional functions from those described above.

In the case of multiple independent approaches, the pre-module routing may make the same determination that the process should route manually or in an automated approach and if the automated route is selected, then all automated processes may be simultaneously performed and returned to the post-routing module which can either combine the results from the automated processes in order to generate a final result or may use voting or some form of agreement mechanism to select a single result or to make a routing determination. In either event, the result may be evaluated and passed to the output or to the manual process for review. For example, multiple independent mesh segmentation approaches may be performed. If they are all in agreement, then this could indicate that the result is good and one representative output should be passed to the module outputs. If the results showed substantial disagreement, then the post-routing module may determine that the result is poor and pass it to the manual process.

For some examples, the pre-module routing may examine the inputs based on dental anatomy, doctor preferences, clinical knowledge, etc. to identify an automated process that is best suited for the particular inputs. This single processing module (e.g., treatment plan generating module) may then process the inputs and pass the results on to the post-process routing. Alternatively, multiple specialized automation processes may be used; for example, multiple independent approaches for a particular type of input may be used.

Figure 6:
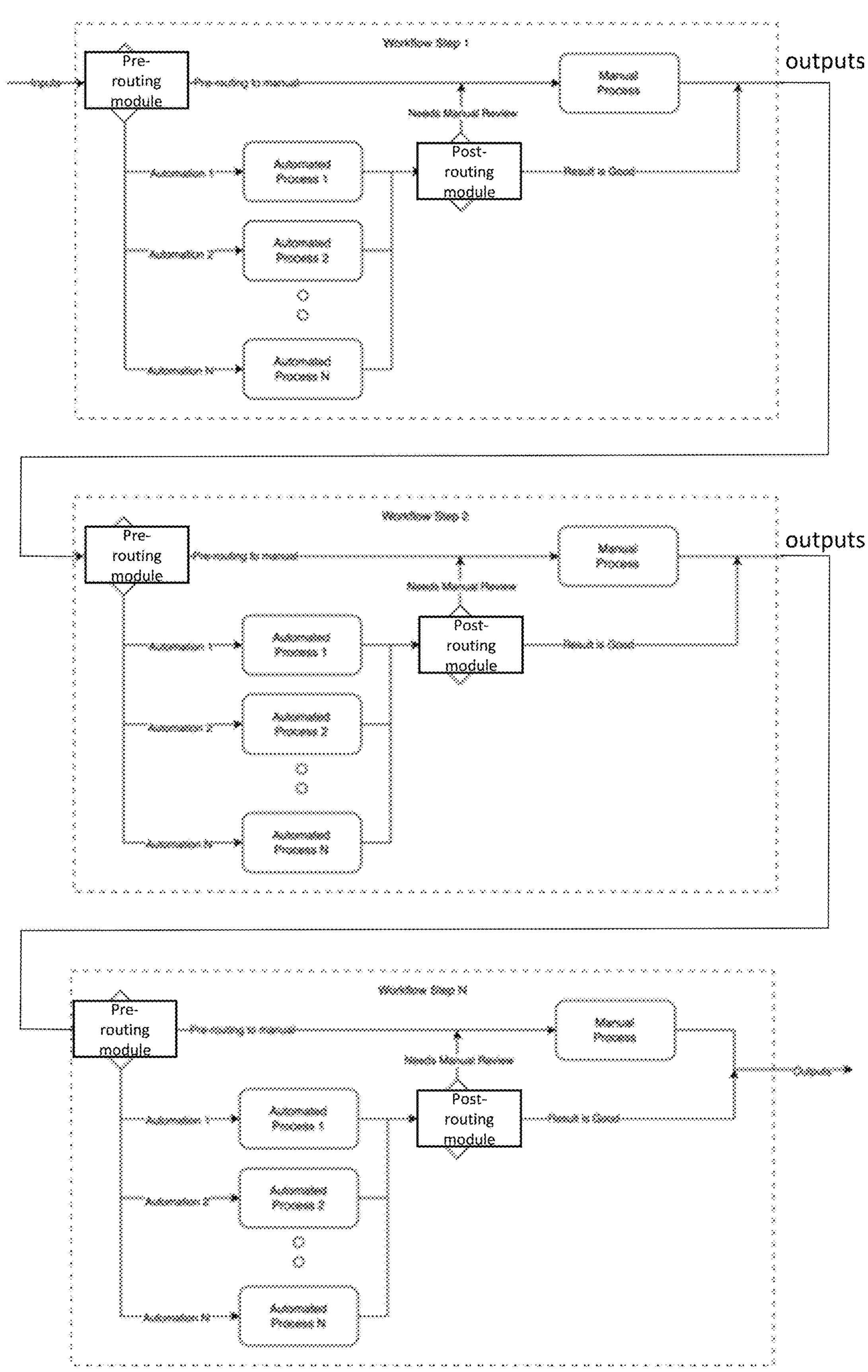
FIG. 6 schematically illustrates an example of a hybrid automated/manual workflow having both parallel and sequential processes.

FIG. 4 illustrates a hybrid manual/automation approach with multiple automations. As can be seen in FIGS. 2-4, a simple process step in a manual workflow can be converted into a more complicated, but more automated, hybrid workflow. For example, a simple linear workflow as shown in FIG. 5 can be converted into the more automated, but conceptually identical hybrid workflow shown in FIG. 6.

The workflows described herein including pre-routing and/or post-routing modules may be scalable and may be rapid to deploy; these methods and apparatuses may also allow for enhancement via automation. In addition, these methods and apparatuses ma allow the use of multiple automation processes for a single manual process, either using a routing decision based on dental/clinical/etc. information, or by combining the results, or using the multiplicity of results to determine the overall quality of the automated processes.

FIG. 7 illustrates one method for processing a dental workflow for a dental treatment of a patient by a dental professional 700. The method may include determining, in a pre-routing module, if one or more processes should be performed on a digital dental model either manually or automatically 701. Examples of this step are provided in greater detail below. The dental workflow may be any appropriate workflow, including treatment planning for tooth alignment using a series of aligners, treatment planning for restorative, etc. If the pre-routing module determines that the automated process (e.g., treatment planning, and/or component parts of treatment planning, such as segmentation, collision detection, etc.) may be performed automatically, then the method or apparatus may automatically perform any of the one or more processes on the digital dental model to generate an output workflow 703. If not appropriate, the method may otherwise indicate that the process should be manually performed (e.g., by an output). Following the automatic processing (e.g., treatment planning or component portion), a post-routing module may determine if the automatically determined output workflow contains one or more parameter values that is outside of a range of parameter values 705. If the post-routing module indicates that the output workflow is acceptable, the output workflow (e.g., automatically generated treatment plan) may be transmitted to an indicator to manually perform the one or more processes if the post-routing module determines that one or more parameters values is outside of the range of parameter values 707. If the post-routing module determines that one or more parameters values is outside of an acceptable range of parameter values the method or apparatus may signal or otherwise indicate that the manual process should be used and either an entirely new workflow be generated, or a modified version of the automatically generated workflow may be prepared. For example, optionally, in cases where the post-routing module determines that one or more parameters values is outside of the acceptable range of parameter values a workflow modification module may be used to modify the automatically generated workflow 709.

Pre-Routing Module

In some examples the apparatus or method may include only a pre-routing module, without a post-routing module. For example, FIG. 8 schematically illustrates a schematic of a method for processing a workflow (e.g., dental treatment plan) for a patient in a case in which the dental professional submits a patient-specific prescription for treating a patient's dentition.

For example, when a doctor elects to use an automated treatment planning module ("automated setup"), the case may proceed directly to automatic setup without technician intervention. Most of the time, the doctor quickly receives a high-quality setup that meets the doctor's intention; however, in a small but significant number of cases the resulting workflow may not meet the doctor's expectations. In these cases, the doctor may be dissatisfied and may reject the case. In some instances, a technician can fix the issues, however in other instances, the case must be fully reworked using our manual processes.

Figure 8:
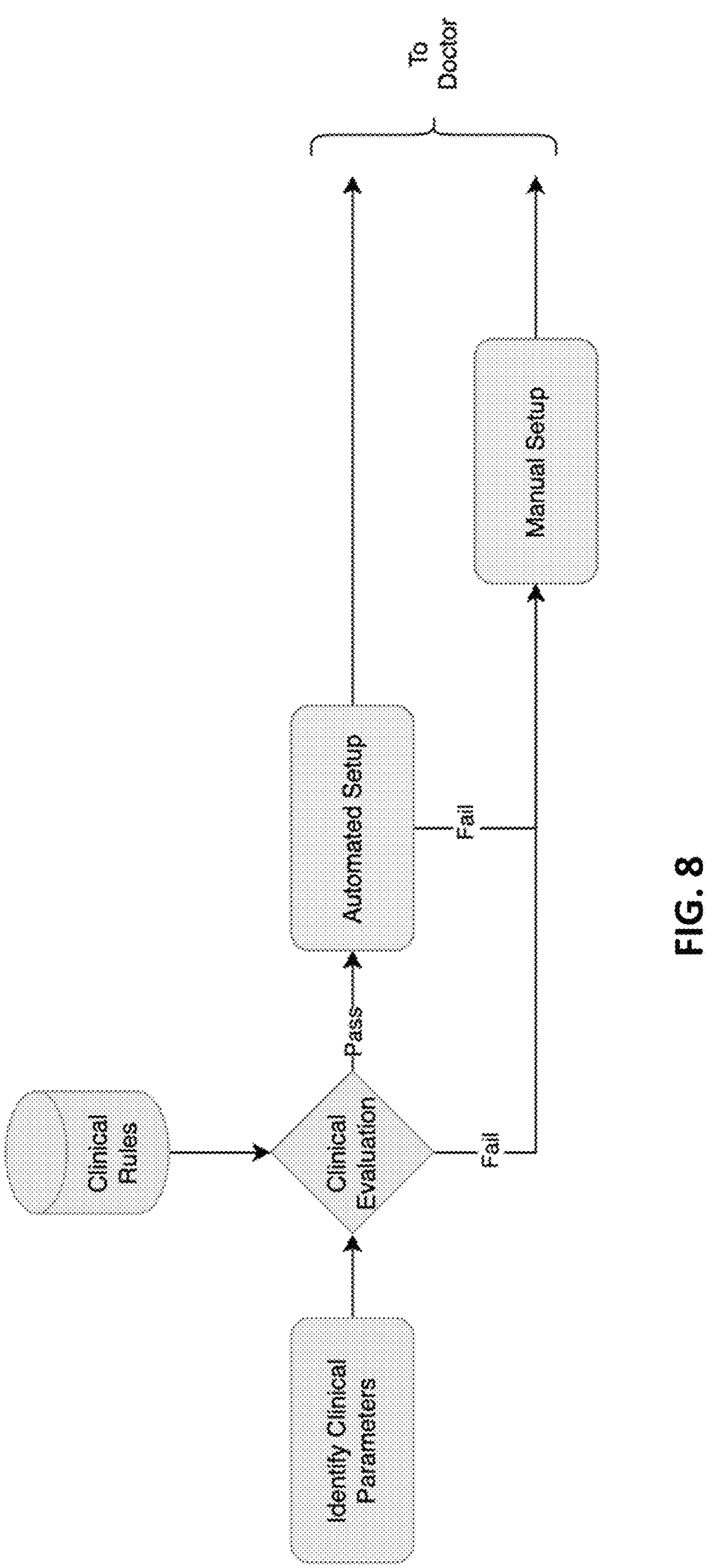
FIG. 8 schematically illustrates one example of a dental workflow including a pre-routing module.

Thus, in any of these methods and apparatuses a routing decision may be included prior to the automated case setup, e.g., the pre-routing module (including, in FIG. 8, the identifying clinical parameters, clinical rules and clinical evaluation). The routing decision (pre-routing module) may evaluate the clinical factors of the case and determine whether it is suitable for the current version of automated setup. If the case is suitable, it may be routed to automated setup and if not, it may be routed to a manual process (e.g., a CAD Designer/Technician) for manual case setup.

In some examples the pre-routing module may include a form of expert system in which the relevant clinical rules are maintained as a separate component (e.g., updatable clinical rule database) and updated versions of the automated setup permits maintenance of the clinical rules.

Alternatives to the clinical routing (e.g., using a pre-routing module) method shown in FIG. 8 may include always automatically generating the treatment plan, which may minimize the technician time because only unaccepted setups would be routed to the technicians. However, this alternative exposes poor quality setups to the doctors, which may increase the time needed from the doctor and may decrease the doctor's satisfaction with the process. Alternatively, the case may always be sent to the automated setup and after the setup an evaluation of setup quality may be made. However, this may be very time intensive. The methods and apparatuses described herein may instead focus on the INPUT to the automated assessment rather than the output. Thus, changes to the automated case setup may not require the system or method to rebuild a model or predictor.

FIG. 9 illustrates one example of a method of processing workflow for a dental treatment of a patient 900. In this example, the method may include determining, in a pre-routing module, if one or more processes (e.g., dental treatment planning to align teeth using a series of aligners) should be performed automatically (e.g., by an automated treatment planning module) according to a patient-specific prescription 901. The pre-routing module may identify clinical parameters from the patient-specific prescription and the digital dental model of the patient's dentition (e.g., geometric features of one or more teeth of the digital dental model of the patient's dentition, a relative position of the patient's teeth from the digital model of the patient's dentition, a type of procedure requested in the patient-specific prescription, an age of the patient, and an identifier of the dental professional submitting the patient-specific prescription) 903. The pre-routing module may also access clinical rules from an undatable clinical rule database (e.g., rules related to one or more of: dental morphology of the patient's teeth, one or more characteristics of the automated treatment planning module, and the identity of the dental professional) 905, and may apply (e.g., by comparing) the clinical rules to the clinical parameters identified from the digital dental model and the patient-specific prescription, e.g., using an expert system to evaluate the application of the clinical rules to the clinical parameters, to determine if the process should be automatically or manually performed 907.

Based on the output of the pre-routing module, the method may generate the output workflow (e.g., dental treatment plan) using the automated process(s) (e.g., the automated treatment planning module) when the pre-routing module indicates that the dental treatment plan should be automatically generated or may transmit an indicator to manually generate the output workflow when the pre-routing module indicates that the output workflow should not be automatically generated 909.

Figure 10:
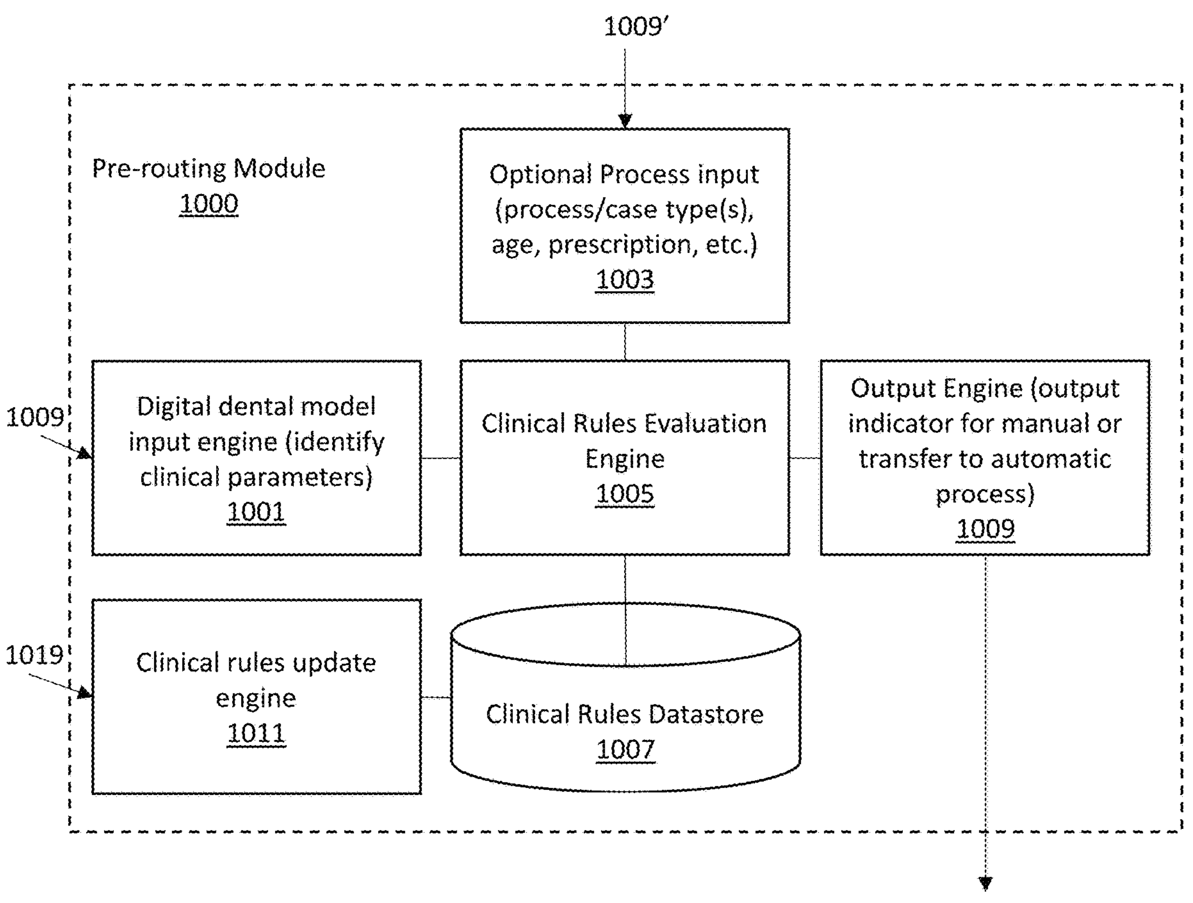
FIG. 10 shows a schematic illustration of a pre-routing module that may be part of a system as described herein.

FIG. 10 schematically illustrates a pre-routing module 1000 that may be used as part of a system as described herein. In general, the pre-routing module may include inputs, such as the digital dental module input engine 1001, which may identify clinical parameters from the digital model of the patient's dentition, and the process input engine 1003, which may receive the prescription and/or associated information (e.g., patient age, case type, etc.). In general, the pre-routing module may include one or more engines and datastores. A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors, or a first engine and a second engine can share one or more processors with one another or other engines. Depending upon implementation-specific or other considerations, an engine can be centralized, or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The systems and modules described herein may include or be part of (or contained on) a computer-readable medium. The computer-readable medium may include any computer-readable medium, including without limitation a bus, a wired network, a wireless network, or some combination thereof.

In FIG. 10, the pre-routing module may further include a clinical rules evaluation engine 1005 for analyzing/comparing the parameters identified from the patient's digital dental model to the clinical rules from the clinical rules datastore 1007. As mentioned, the module may also include a clinical rules update engine 1011 for updating (based on input 1019) the clinical rules datastore. The module may also include an output engine 1009 that is configured to output an indicator indicating that manual processing should be used if the clinical rules evaluation engine 1005 determines that the parameters from the digital dental model are in breach of the rules.

In general, the pre-routing module may include a component to identify one or more clinical parameters for a particular case (e.g., the digital model input engine 1001). Identified clinical parameters may include: clinical measurements of the case based on the geometric features in the segmented scan (e.g., tooth measure-like functionality, which may represent how 'normal' the patient's teeth are within expected parameters), the case type, product type, age type, etc.; case-specific prescription (e.g., data specific to the prescribing dental practitioner), and how relevant the prescription is, and specific details about the automated processing module.

The clinical rules may comprise a set of rules that is based on clinical expertise and reflects current explicit knowledge of cases in which an automated setup (automated processing module) is likely to produce a poor result. Sample clinical rules could consider any combination of the automated processing module in use, the case prescription, and clinical measurements such as: worn teeth, Bolton discrepancies (e.g. peg lateral incisors), implant cases in which space must be preserved, posterior spaces due to missing premolars, primary teeth, dentition type, orthognathic surgery, CR (centric relation)/CO (centric occlusion) discrepancy, scissor bite, planned $2^{nd}$ molar extraction, and/or excessive crowding.

The clinical rules evaluation (clinical evaluation) engine may compare the clinical parameters against the clinical rules and may make a rule-based determination if the case should route to manual or automated setup. Thus, the clinical rules evaluation could use any form of expert-system rule evaluation (e.g., scoring each rule and routing based on a threshold; rule-based flow chart; or a simple system where the first rule indicating manual setup causes the case to route to a manual setup), and may include an agent (e.g., machine learning/artificial intelligence agent), which may be trained on the rules from the updatable clinical rules datastore.

The methods and apparatuses described herein may achieve a significant cost benefit while minimizing the presentation of poor quality workflows (treatment plans) shown to doctors.

Post-Routing Module

In some examples the apparatuses or methods described herein may include only a post-routing module, without a pre-routing module. These methods and apparatuses may use an additional source of information as doctor comments and special instructions that may significantly improve success rate of automatic treatment quality assessment. An automatic analysis of a workflow (e.g., a treatment plan) may be performed, and may determine that the workflow is outside of an expected set of values for one or more parameters, based on clinical criteria. For example, numerical and/or clinical parameters may be analyzed, such as overbite, overjet and high deviations are detected. Based on the analysis in the post-routing module, the post-routing module may output instructions to pass or fail the workflow. If the workflow fails, It may be forwarded on for manual attention, including for manual inspection and/or for manually redoing (or revising) the automated workflow.

The automatic treatment assessment approach may be improved as descried herein by considering human readable text while performing quality assessment. Sometimes doctors explicitly request the parameters to go beyond clinically accepted boundaries and this leads to false-positives automatic routings to inspection. The methods and apparatuses described herein may include Natural language processing (NLP) analysis of the prescribing dental practitioner's instructions to improve success rate.

Figure 11:
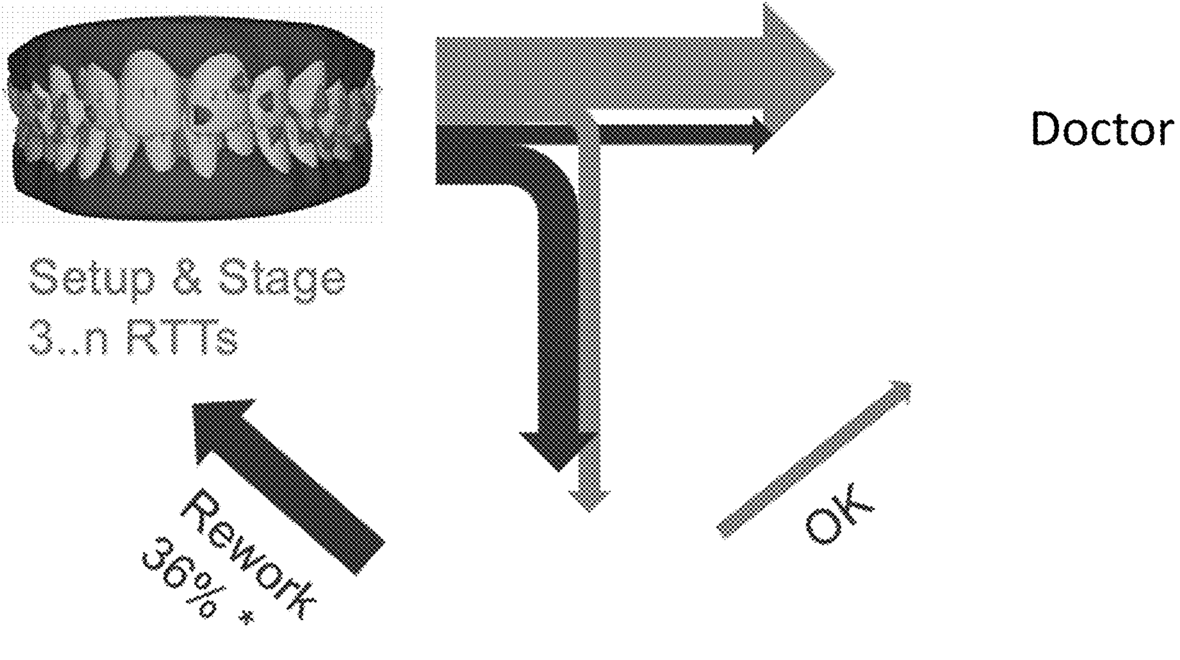
FIG. 11 schematically illustrates one example of a dental workflow showing the effect of a post-routing module.

For example, FIG. 11 illustrates an example in which the post-routing module is used as described herein. In FIG. 11, the workflow (treatment plan) is initially automatically generated a post-routing module is used to analyze the output; based on this review, the majority of workflows are passed on to the doctor, while a subset is passed downwards to an inspector (technician) that may then manually review them. A subset of these is approved manually and passed on to the doctor, while the majority are either reworked or manually redone, as shown, however, the use of an additional NLP model for analysis of doctor comments may further refine these benefits. For example, the workflow may be analyzed by the post-routing module including logic based on parameters extracted from the digital dental model (e.g., to determine that the case is incorrectly set up because of tooth movement parameter X that is out of bounds, e.g., X_min, X_end). In this example, the logic of the post-routing module may be based, at least in part, on Tooth Measure parameters analysis finds out that the case is incorrectly set up because of TM parameter X that is out of bounds (X_min, X_end). The NLP logic may indicate that the dental practitioner explicitly asks in comments in human readable form that X should be out of bounds (X_min, X_end). The NLP logic may mark the case as not containing any treatment problems.

FIG. 12 schematically illustrates a method for processing a workflow for a dental treatment of a patient when a dental professional submits a patient-specific prescription. In FIG. 12, the method 1200 may include receiving an automatically-generated workflow (e.g., dental treatment planning to align teeth using a series of aligners, etc.) that was generated by an automated treatment planning module) according to a patient-specific prescription 1201. The method may further determine, in a post-routing module, if the workflow contains one or more values that is/are outside of a range of acceptable parameter values 1203. For example, the method may identify parameters (e.g., tooth movement parameters) from the workflow 1205, and compare the parameters to a set of acceptable parameter values (retrieve the acceptable parameter values from a datastore of acceptable values) 1207.

If any of the parameters are outside of the range of acceptable vales, determine (with a false-positive verification module) if these parameters are intended to be exceptions based on the prescriber's intent 1209. The method may further include reviewing the human-readable (natural language, e.g., prescriber-written) prescription text using a trained machine-learning agent to identify exceptions for any of the parameter's outside of the range of acceptable values in the prescriber's instructions 1211. Finally, the output for the method may be an indicator that the workflow (e.g., treatment plan) should be redone manually or with manual assistance if (1) there are one or more parameters outside of the range of acceptable values and (2) the one or more parameters are not exceptions based on the prescriber's written instructions 1213.

Figure 13:
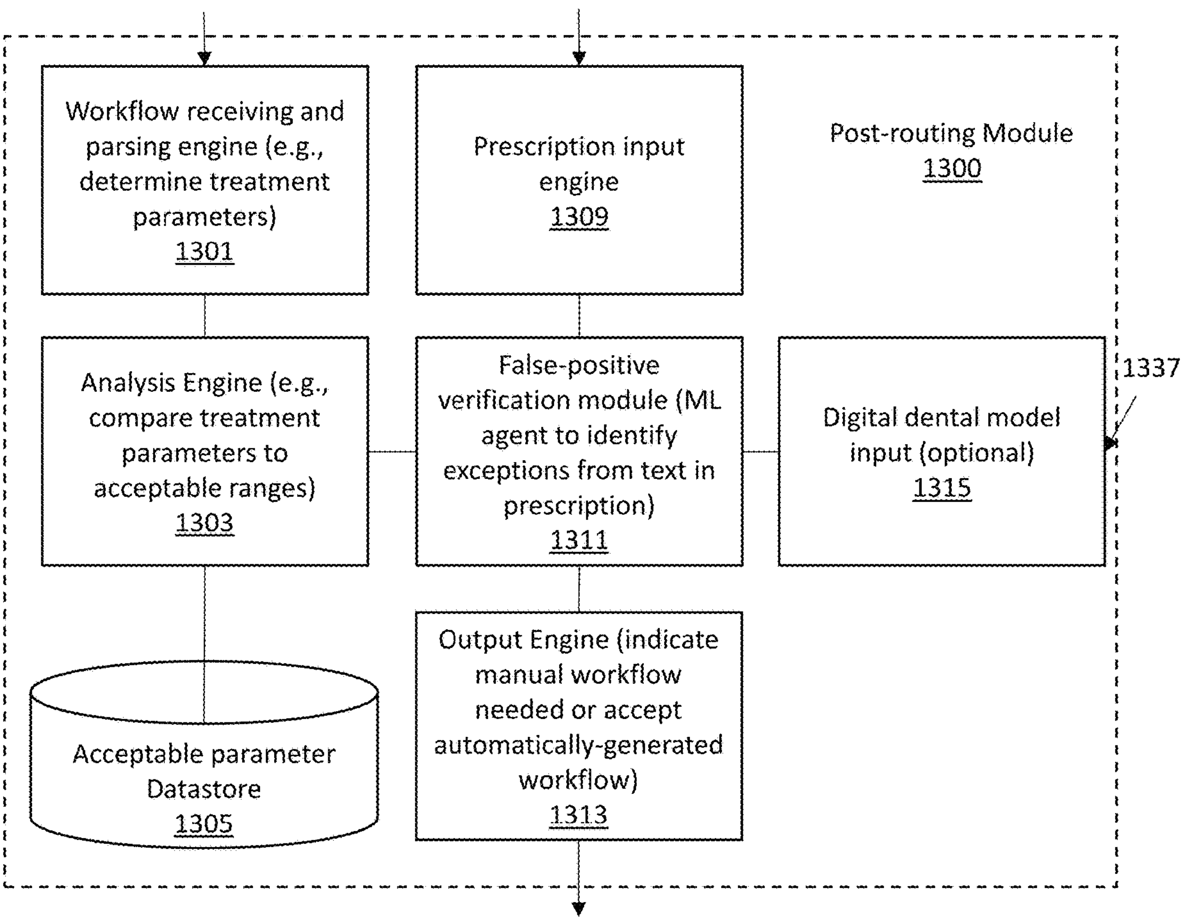
FIG. 13 shows a schematic illustration of a post-routing module that may be part of a system as described herein.

FIG. 13 illustrates an example of a post-routing module 1300. In this example, the module includes a workflow receiving and parsing engine 1301 that may determine treatment parameters as mentioned above. An analysis engine (e.g., configured to compare treatment parameter to acceptable ranges from an acceptable parameter datastore 1305) may be included in the post-routing module. The prescription input engine 1309 may allow input and parsing of the intended prescription. A false-positive verification model 1311, which may include or operate a machine learning agent that is trained to identify if any parameters that is outside of an acceptable range, as mentioned above, is otherwise still acceptable based on the text of the prescription (including natural langue instructions or comments from the prescriber). The post-routing module may also include an output engine 1313 that may indicate when manual oversight, review and/or revision of the workflow is necessary. The module may also (optionally) include a digital dental model input 1315.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for processing a dental workflow for a dental treatment and one or more dental appliances for a patient, the method comprising:

determining, in a pre-routing module, if one or more processes in generating an output workflow should be performed on a digital dental model either manually or automatically, based on comparing patient-specific clinical parameters against clinical rules, wherein the clinical rules are based on a likelihood of clinical parameters producing a poor dental workflow;

automatically performing any of the one or more processes on the digital dental model to generate the output workflow when the pre-routing module indicates that the one or more processes should be automatically performed;

determining, in a post-routing module, if the output workflow contains one or more output parameter values that is outside of a range of acceptable output parameter values;

transmitting an indicator to manually perform the one or more processes if the post-routing module determines that one or more output parameters values is outside of the range of acceptable output parameter values;

modifying the output workflow based on the one or more processes being manually or semi-manually performed; and fabricating the one or more dental appliances in accordance with the modified output workflow.

2. The method of claim 1, further comprising determining, in a false-positive verification module, if the one or more output parameter values that is outside of the range of acceptable output parameter values is an exception based on an automatic review of a set of dental treatment instructions provided by a dental professional associated with the set of dental treatment instructions written in a natural language text; wherein transmitting the indicator to manually perform the one or more processes comprises transmitting the indicator only if the post-routing module determines that the one or more output parameters values is outside of the range of acceptable output parameter values and if the false-positive verification module does not identify the exception.

3. The method of claim 2, wherein the automatic review comprises using a machine agent to identify the exception for the one or more output parameter values from the natural language text of the set of dental treatment instructions.

4. The method of claim 2, wherein the false-positive verification module is part of the post-routing module.

5. The method of claim 1, wherein the clinical rules are maintained in an updatable clinical rule database.

6. The method of claim 5, wherein the clinical rules is related to one or more of: a dental morphology, a treatment to be performed on the patient's teeth represented by the digital dental model, one or more characteristics of the automated process, and an identifier of a dental professional associated with the treatment.

7. The method of claim 1, further comprising transmitting an indicator to manually perform any of the one or more processes that the pre-routing module indicates should not be automatically performed.

8. The method of claim 1, wherein the post-routing module accesses a data set of the acceptable output parameters values to determine if the one or more output parameters values is outside of the range of acceptable output parameter values.

9. A method for processing a dental workflow for a dental treatment and one or more dental appliances for a patient, the method comprising:

determining, in a pre-routing module, if one or more processes in generating an output workflow should be performed on a digital dental model either manually or automatically, based on comparing patient-specific clinical parameters against clinical rules, wherein the clinical rules are based on a likelihood of clinical parameters producing a poor dental workflow;

automatically performing any of the one or more processes on the digital dental model to generate the output workflow when the pre-routing module indicates that the one or more processes should be automatically performed;

determining, in a post-routing module, if the output workflow contains one or more output parameters values that is outside of a range of acceptable output parameter values;

determining, in a false-positive verification module, if the one or more output parameter values that is outside of the range of acceptable parameter values is an exception based on an automatic review of a set of dental treatment instructions provided by a dental professional associated with the set of dental treatment instructions written in a natural language text;

transmitting an indicator to manually perform the one or more processes if the post-routing module determines that the one or more output parameters values is outside of the range of acceptable output parameter values and if the false-positive verification module does not identify the exception;

modifying the output workflow based on the one or more processes being manually or semi-manually performed; and fabricating the one or more dental appliances in accordance with the modified output workflow.

10. A method for processing a dental workflow for a dental treatment and one or more dental appliances for a patient, the method comprising:

determining, in a pre-routing module, if one or more processes in generating an output workflow should be performed on a digital dental model either manually or automatically, based on threshold clinical parameters resulting from the application of one or more clinical rules that are maintained in an updatable clinical rule database to the digital dental model, and comparing the threshold clinical parameters to patient-specific clinical parameters, wherein the clinical rules are based on a likelihood of generating an acceptable output workflow when the one or more processes are automatically performed, wherein the one or more clinical rules is related one or more of: a dental morphology, a treatment to be performed on the patient's teeth represented by the digital dental model, one or more characteristics of the automated process, and an identifier of a dental professional associated with the treatment;

automatically performing any of the one or more processes on the digital dental model to generate the output workflow when the pre-routing module indicates that the one or more processes should be automatically performed;

determining, in a post-routing module, if the output workflow contains one or more output parameters values is outside of a range of acceptable output parameter values;

transmitting an indicator to manually perform the one or more processes if the post-routing module determines that the one or more output parameters values is outside of the range of acceptable output parameter values;

modifying the output workflow based on the one or more processes being manually or semi-manually performed; and fabricating the one or more dental appliances in accordance with the modified output workflow.

11. A system, the system comprising:

one or more processors; and a memory coupled to the one or more processors, the memory storing computer-program instructions, that, when executed by the one or more processors, perform a computer-implemented method comprising:

determining, in a pre-routing module, if one or more processes in generating an output workflow should be performed on a digital dental model either manually or automatically, based on threshold clinical parameters resulting from the application of clinical rules to the digital dental model, and comparing the threshold clinical parameters to patient-specific clinical parameters, wherein the clinical rules are based on a likelihood of generating an acceptable output workflow when the one or more processes are automatically performed;

automatically performing any of the one or more processes on the digital dental model to generate the output workflow when the pre-routing module indicates that the one or more processes should be automatically performed; and determining, in a post-routing module, if the output workflow contains one or more output parameters values is outside of a range of acceptable output parameter values;

transmitting an indicator to manually or semi-manually perform the one or more processes if the post-routing module determines that the one or more output parameters values is outside of the range of acceptable output parameter values;

modifying the output workflow based on the one or more processes being manually or semi-manually performed; and fabricating one or more dental appliances in accordance with the modified output workflow.

12. The system of claim 11, wherein the computer-implemented method further comprises determining, in a false-positive verification module, if the one or more output parameter values that is outside of the range of acceptable output parameter values is an exception based on an automatic review of a set of dental treatment instructions provided by a dental professional associated with the set of dental treatment instructions written in a natural language text; wherein transmitting the indicator to manually or semi-manually perform the one or more processes comprises transmitting the indicator only if the post-routing module determines that the one or more output parameters values is outside of the range of acceptable output parameter values and if the false-positive verification module does not identify the exception.

13. The system of claim 12, wherein the automatic review comprises using a machine agent to identify the exception for the one or more output parameter values from the natural language text of the set of dental treatment instructions.

14. The system of claim 12, wherein the false-positive verification module is part of the post-routing module.

15. The system of claim 11, wherein the clinical rules are maintained in an updatable clinical rule database.

16. The system of claim 15, wherein the clinical rules is related one or more of: a dental morphology, a treatment to be performed on the patient's teeth represented by the digital dental model, one or more characteristics of the automated process, and an identifier of a dental professional associated with the treatment.

17. The system of claim 11, further comprising transmitting an indicator to manually perform any of the one or more processes that the pre-routing module indicates should not be automatically performed.

18. The system of claim 11, wherein the post-routing module accesses a data set of the acceptable output parameters values to determine if the one or more output parameters values is outside of the range of acceptable output parameter values.

19. The method of claim 1, wherein the comparing comprises comparing threshold clinical parameters to the patient-specific clinical parameters, wherein the threshold clinical parameters result from the application of the clinical rules to the digital dental model.

20. The method of claim 1, wherein determining if the output workflow contains one or more output parameter values that is outside of a range of acceptable output parameter values comprises determining that the one or more processes of the output workflow should be manually performed.

21. The method of claim 1, wherein determining if the one or more processes should be performed comprises evaluating a quality of an input for generating the output workflow, and wherein determining if the output workflow contains one or more output parameter values that is outside of the range of acceptable output parameter values comprises determining whether to modify the output workflow by evaluating a quality of the one or more output parameter values.

* * * * *